United States Patent
Kuznetsova et al.

(10) Patent No.: US 7,842,730 B2
(45) Date of Patent: Nov. 30, 2010

(54) MEDICAL EMULSION OF PERFLUORORGANIC COMPOUNDS AND METHOD FOR THE PRODUCTION THEREOF

(75) Inventors: Irina Nikolaievna Kuznetsova, per. Ulyana Gromova, 8-67, RU-191036 St. Petersburg (RU); Evgeny Ilich Maievsky, Microraion AB, 1-17, RU-142290 Puschino, Moskovskaya obl. (RU)

(73) Assignees: Evgeny Pavlovich Germanov, Moscow (RU); Irina Nikolaievna Kuznetsova, St. Petersburg (RU); Evgeny Ilich Maievsky, Puschino, Moskovskaya obl. (RU)

( * ) Notice: Subject to any disclaimer, the term of this patent is extended or adjusted under 35 U.S.C. 154(b) by 641 days.

(21) Appl. No.: 10/591,411

(22) PCT Filed: Feb. 7, 2005

(86) PCT No.: PCT/RU2005/000058

§ 371 (c)(1),
(2), (4) Date: Sep. 1, 2006

(87) PCT Pub. No.: WO2005/089739

PCT Pub. Date: Sep. 29, 2005

(65) Prior Publication Data

US 2007/0197475 A1    Aug. 23, 2007

(30) Foreign Application Priority Data

Mar. 1, 2004 (RU) ............................... 2004106722

(51) Int. Cl.
*A01N 43/36* (2006.01)
*A01N 29/02* (2006.01)
*A61K 31/40* (2006.01)
*A61K 31/02* (2006.01)
*C07C 19/08* (2006.01)
*C07C 22/00* (2006.01)
*C07C 25/13* (2006.01)
*C07C 19/00* (2006.01)
*C07C 21/00* (2006.01)
*C07C 21/18* (2006.01)

(52) U.S. Cl. ...................... 514/757; 514/424; 514/758; 514/759; 514/760; 514/761; 570/131; 570/134; 570/137; 570/141

(58) Field of Classification Search ............... 514/78, 514/315, 672, 759, 761, 424, 757, 758, 760; 570/131, 134, 137, 141
See application file for complete search history.

(56) References Cited

U.S. PATENT DOCUMENTS

| | | | |
|---|---|---|---|
| 3,778,381 A | 12/1973 | Rosano et al. | |
| 4,866,096 A | 9/1989 | Schweighardt | |
| 5,344,393 A * | 9/1994 | Roth et al. | 604/4.01 |
| 5,374,624 A | 12/1994 | Segel | |
| 5,733,526 A * | 3/1998 | Trevino et al. | 424/9.52 |
| 6,113,919 A * | 9/2000 | Reiss et al. | 424/400 |

FOREIGN PATENT DOCUMENTS

| | | |
|---|---|---|
| RU | 2 088 217 | 8/1997 |
| RU | 2 162 692 | 2/2001 |
| RU | 2162692 C1 * | 2/2001 |
| RU | 2 199 311 | 2/2003 |
| RU | 2 200 544 | 3/2003 |
| RU | 2 200 582 | 3/2003 |
| SU | 797546 | 2/1977 |

OTHER PUBLICATIONS

Ganong, Review of Medical Physiology, 1991, Appleton & Lange, 17th ed., p. 221-222.*
J.G. Rieses et al. Physiological Activity of fluorine-containing Compounds (Tests and Clinical Examinations), collection of scientific works, Puschtschino, 1995, p. 73-90.
J.G. Rieses, Chem. Rev., 2001, V. 101, No. 9, p. 2797-2799.
Graph A (Sheet 1 of 1).
Graph B (Sheet 1 of 1).
Chart A (Sheet 1 of 1).

* cited by examiner

Primary Examiner—Sreeni Padmanabhan
Assistant Examiner—Sarah Pihonak
(74) Attorney, Agent, or Firm—Pauley Petersen & Erickson

(57) ABSTRACT

Medicine, in particular medications for treating blood losses, hypoxic and ishemic states, for improving a blood oxygen supply and for preserving isolated perfused organs and tissues. The inventive medical emulsion of perfluororganic compounds includes rapidly excretable perfluororganic compounds such as perfluordecalin, perfluoractilbromide, a perfluoroganic additive embodied in the form of a mixture of perfluorinated tertiary amines and phospholipids in the form of a water-salt dispersion. The perfluordecalin and perfluoractilbromide are contained in the composition of the rapidly excretable perfluororganic compounds at a ratio ranging from 10:1 to 1:10. The mixture of perfluorinated tertiary amines is embodied in the form of the mixture of perfluorotpripropylamine and the co-products thereof: cis- and trans-isomers perfluor-1-propyl 3,4-dimethylpirrolidone and perfluor-1-propyl-4-methhylpiperidine. The inventive method for producing the emulsion includes producing the water-salt dispersion of phospholipids, in homogenizing the perfluororganic compounds therein at a high pressure and in sterilization of the final emulsion. The storage life of the inventive emulsion in the unfrozen state thereof at a temperature of +4° C. is equal to at least 6 months during which the biocompatibility of the emulsion with a biological medium (blood, plasma or serum) is preserved.

21 Claims, 1 Drawing Sheet

A  B

Figure 1:
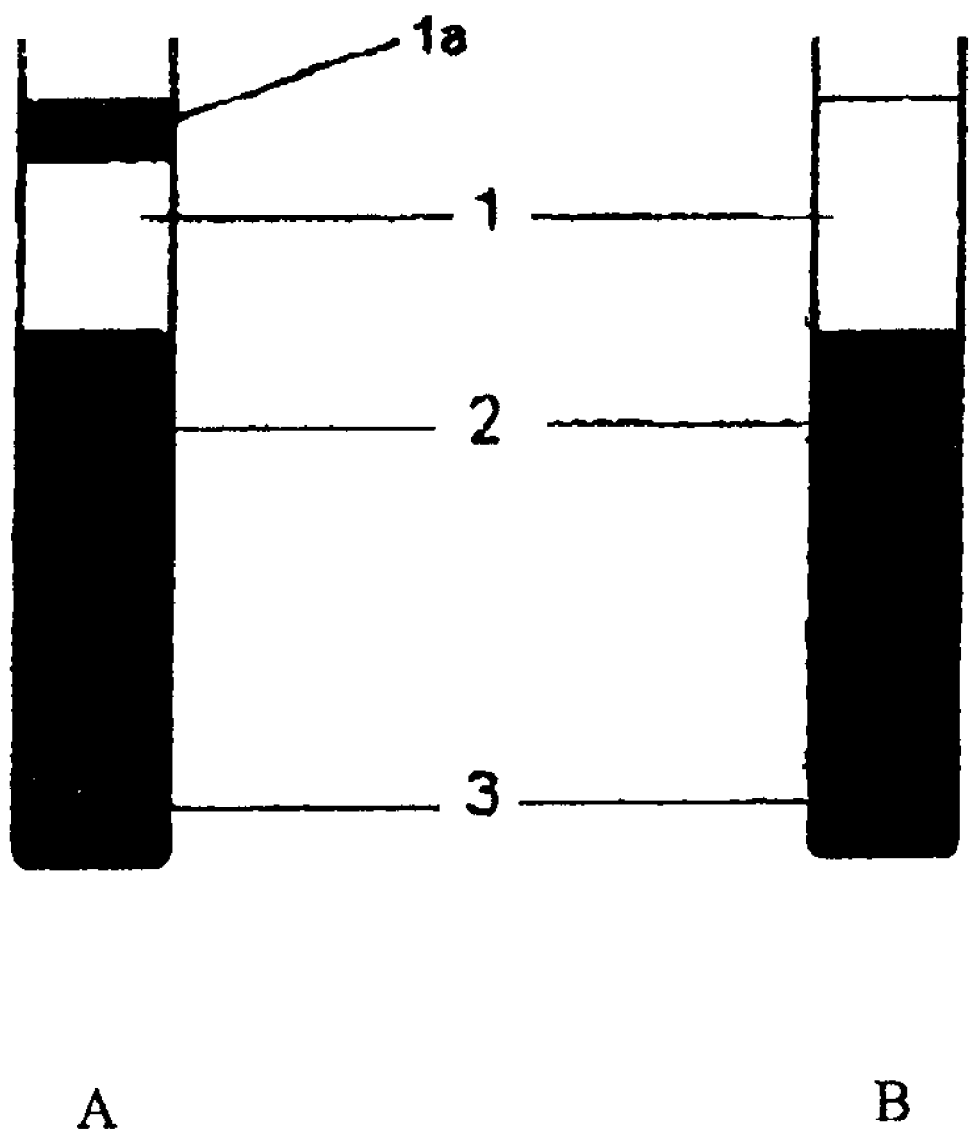

MEDICAL EMULSION OF PERFLUORORGANIC COMPOUNDS AND METHOD FOR THE PRODUCTION THEREOF

BACKGROUND OF THE INVENTION

1. Field of the Invention

This invention relates to the field of biophysics and medicine, in particular to pharmaceuticals for the treatment of blood losses, hypoxia and ischaemic conditions and also for improving the blood oxygen transport and the preservation of isolated perfusing organs and tissues.

2. Discussion of Related Art

List of abbreviations, references, units and terms

| | |
|---|---|
| Surfactants | surface-active substances |
| P-268, F-268 | Proxanol 268, Pluronic 268 |
| PFD | perfluorodecaline |
| PFMHP | perfluoromethylcyclohexylpiperidine |
| PFOB | perfluorooctylbromide |
| Fl | organic fluid which represents a mixture of perfluorotripropylamine and its coproducts, cis- and trans-isomers: perfluoro-1-propyl-3,4-dimethylpyrrolidone and perfluoro-1-propyl-4-methylpiperidine. |
| PFCs | fluorocarbons, fluorocarbon compounds |
| PFTBA | perfluorotributylamine |
| PFTPA (PAF-3) | perfluorotripropylamine |
| Soya-P | soya phospholipids |
| Egg-P | egg phospholipids |
| n | wavelength exponent |
| Cv | volumetric content of fluorocarbons in emulsion (ml/dl) |
| a | average particle size |
| λ | wavelength |
| Ip | reactogenity index |

The success in developing infusion media, which contain emulsions of fluorocarbon compounds, depends largely upon the physical-chemical properties of selected PFCs and emulsions based on these PFCs and also upon the production method.

PFCs for medicinal purposes represent fluorocarbon compounds of different classes. Externally, these are clear, colorless and odorless liquids with a very high density, approximately twice as heavy as water. An abnormally strong C—F bond (485.6 KJ/mol) leads to the fact that the intermolecular forces of these compounds are very weak. Weak intermolecular forces are manifested in their abnormally strong ability to dissolve gases, amongst them also blood gases.

The PFCs are characterized as a result of the strong C—F bond by chemical inactivity. They dissolve in water with difficulty and do not form the metabolic basis in organisms. The chemical inactivity of the PFCs cannot be equated to a biological inactivity. With intravenous injection of the emulsions on a PFC basis, these emulsions are retained in organs and tissues, the dwell time being dependent upon the nature of the PFC and the dose of the emulsion.

Investigations into the biological properties of perfluorinated compounds of different classes show that the elimination rate depends upon a series of connected physical-chemical parameters, namely upon the structure and the molecular weight, the boiling temperature, the vapor pressure and the critical dissolving temperature in hexane ($T_{critical}$) $T_{critical}$ is that temperature at which the same volumes of the compound which is to be examined and of hexane mix. $T_{critical}$ is considered as a value of the relative PFC solubility in lipids, which value characterizes the rate of passage into membranes. The lower $T_{critical}$ is, the better the compound dissolves in lipids and the more rapidly it is eliminated from the organism. In Table 1, physical-chemical parameters are indicated which serve as selection criteria of PFCs for medicinal application.

TABLE 1

Values for the critical solution temperature in hexane ($T_{critical}$), the vapor pressure (P) and the half-decomposition time ($t_{1/2}$) of different compounds [1].

| Perfluorinated compounds | Molar weight | $T_{critical}$ | P, mm QS (37°) | Half-decomposition time $t_{1/2}$ 24 hours |
|---|---|---|---|---|
| bicyclo[4.3.0]nonane | 412 | 13 | 33 | 4 |
| decaline | 462 | 22 | 12 | 7 |
| decahydroacenaphthene | 524 | 24 | 2 | 7 |
| N-(4-methylcyclohexylpiperidine) | 595 | 38 | 1 | 60 (90) |
| 1-propyl-2-methylpiperidine | 483 | 35 | 19 | 24 |
| tripropylamine | 521 | 43 | 17 | 65 |
| tributylamine | 671 | 61 | 1 | 900 |
| dihexylether | 652 | 59 | 2 | 500 |

From the above data a strong correlation between $T_{critical}$ and $t_{1/2}$ can be seen. This correlation is not observed for the vapor pressure. To a great extent $T_{critical}$ and the molecular weight are interconnected. An optimal molecular weight for PFCs is the range between 460 and 520. Overall, all the offered selection criteria for medicinal PFCs are not mutually contradictory, but have a qualitative character. Nowadays, researchers who are involved in the development and examination of perfluorocarbon emulsions are directing their attention to a relatively restricted number of compounds. In Tables 2 and 3, the structural formulae and the physical-chemical main properties of the most widespread PFCs are indicated.

TABLE 2

Structural formulae of the most widespread and promising PFVs

| perfluorodecaline (PFD) mol. wt. 462 | perfluorotripropyl-amine (PFTPA) mol. wt. 521 | perfluorotributylamine (PFTBA) mol. wt. 671 |
|---|---|---|
| 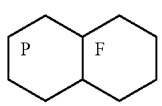 | 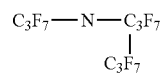 | 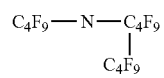 |

TABLE 2-continued

Structural formulae of the most widespread and promising PFVs

| perfluorotrimethyl-bicyclononane mol. wt. 562 | perfluoromethyl-isoquinoline mol. wt. 495 | perfluoromethylcyclohexyl-piperidine mol. wt. 595 |
|---|---|---|
| perfluorooctyl-bromide (PFOB) $CF_3-(CF_2)_6-CF_2Br$ mol. wt. 499 | bis-perfluorobutylethene (F-44E) $C_4F_9-CH=CH-C_4F_9$ mol. wt. 464 | bis-fluorohexylethene (F-66E) $C_6F_{13}-CH=CH-C_6F_{13}$ mol. wt. 664 |

When examining primary biological properties of different PFCs, an important requirement is formulated: the absence of non-identifiable admixtures. Admixtures with unknown properties can distort the true behavioral picture (retention in organs, toxicity, influence on different systems of the organism) of the basic substance when injected intravenously.

TABLE 3

Physical-chemical properties of PFCs which form the basis of medicinal preparations.

| Properties | PFD | PFTPA | PFMHP | PFOB | Perfluorodecylbromide (PFDB) |
|---|---|---|---|---|---|
| Stoichiometric formula | $C_{10}F_{18}$ | $C_9F_{21}N$ | $C_{12}F_{23}N$ | $C_8F_{17}Br$ | $C_{10}F_{21}Br$ |
| Mol. weight, g/mol | 462 | 521 | 595 | 499 | 599 |
| Boiling temperature, °C. | 142 | 131 | 168 | 143 | 180 |
| Vapor pressure, mm QS (37° C.) | 12.7 | 18.0 | 2.0 | 10.5 | 1.5 |
| Critical solution temperature, ($T_{critical}$) °C. | 22 | 44 | 40 | −20 | 7 |
| Oxygen solubility ml/100 ml (vol.-%), (37° C.) | 40 | 45 | 40 | 53 | — |
| Half-decomposition time $t_{1/2}$ | 7 | 65 | 90(60) | 4 | 40 |

Note:
PFD/PFTPA are the basis of the preparation Fluosol-DA;
PFD/PFMHP for the preparation Perftoran;
PFOB/PFDB for the preparation Oxygent.

Liquid PFCs are poor solvents for various water-soluble, biologically active substances. For this reason, the PFCs for application as oxygen transport media are dispersed in an aqueous emulsifier solution until a finely distributed emulsion is obtained.

The ability of PFCs to exchange gases is determined according to the total oxygen content in the emulsion. The oxygen concentration is subject to Henry's Law and is directly proportional to the oxygen pressure. The principle of the physical solubility of the gases in the PFCs extends also to the perfluorocarbon emulsions. The oxygen quantity dissolved in the emulsion depends upon the fluorocarbon phase and not upon the particle size, i.e. the oxygen quantity dissolved in the fluorocarbon emulsion approximates to the values calculated by a summation of the gas quantity values of each phase (oxygen quantity in the aqueous phase plus oxygen quantity in the PFCs). The content of inert gases in the mixture of PFC and plasma is also subject to the summation law of the gas quantity of each phase. Hence, the content of each gas in the emulsion can be calculated according to physical laws of the solubility thereof due to the partial gas pressure and volume ratio of the fractions $PFC/H_2O$. This means that the oxygen content in perfluorocarbon emulsions raises as its partial pressure or its tension ($pO_2$) and the proportion of the fluorocarbon phase raise.

The specific (functional) effect of each preparation when injected into the body is determined by the compatibility of the preparation, which is determined by the $LD_{50}$ value and also by the lack of side-effects which appear mainly as the reactogenity. The size of the $LD_{50}$ value for PFC emulsions depends greatly upon the particle size. The average particle size must not exceed 0.2 μm. An increase in the proportion of large particles (average size over 0.4 μm) of 3% to 10% reduces the $LD_{50}$ value for the mentioned emulsions by a factor of two. Detection of a possible reactogenity of the perfluorocarbon emulsions is one of the most difficult problems which has to be solved when developing a pharmaceutical form based on the perfluorocarbon emulsions for intravenous injection. When using a reactogenity preparation, an allergic reaction can develop in humans which manifests itself in different ways, from slight reddening of the skin to anaphylactic reaction with cessation of breathing and cardiac arrest.

Most researchers are of the opinion that for the most part reactogenity depends upon the nature of the emulsifier which is used for the dispersion of the fluorocarbon basis of the emulsion and which forms a (superficial) absorption layer around the particles. It is believed that the reactogenity of first generation emulsions was caused by the non-ionic block polymer of oxyethylene and polyoxypropylene, Pluronic F 68 (F-68), and that exchange thereof by natural phospholipids completely solves the reactogenity problem. This opinion is not completely correct, because fat emulsions, despite stabilisation by natural phospholipids, possess reactogenity. The reactogenity of the perfluorocarbon emulsions cannot simply be eliminated by the use of phospholipids as emulsifier and stabilizer. In actual fact, it emerged that the reactogenity of the PFC emulsions is effected above all by the surface properties of the emulsified particles, i.e. by the state of the emulsifier layer which stabilizes the particles. In addition to the chemical structure, the nature of the surfactant molecules and the key parameters which determine both the stability of the disperse system and possible secondary reactions, the binding strength of the surfactants with the oil nucleus of the emulsion particles, the position of the molecules on the surface, the density of the packing thereof, the prevalence of the absorption properties relative to proteins and other biologically active molecules which are situated in the bloodstream and finally the size of the emulsion particles play a part. The last parameter should in particular be mentioned. A decrease in the average particle size of the emulsion in the preparation Perftoran, which is only stabilized by the block copolymer polyoxyethylene and polyoxypropylene, Proxanol 268 which is the nearest prototype to F-68, leads to a rapid reduction in the secondary reaction. It is clear from this that in the development, formulation and production method of the emulsions, superficial phenomena (interaction of two heterogeneous systems, emulsion and blood or plasma) play a decisive role in the behavior of the intravenously injected emulsion. The composition of the oil nucleus and also the surfactant which cooperates with the latter should hereby be selected experimentally and also the tenability of the technology used should be tested.

When developing the perfluorocarbon emulsion according to this invention for medicinal purposes and the production method, each formulation and each technological element was examined for biological effect by an animation model. It is known that the reactogenity reaction of rabbits, when injected with perfluorocarbon emulsions, is expressed by a rapid decrease in neutrophilic leucocytes in the peripheral blood. When evaluating possible reactogenity of the perfluorocarbon emulsions, a reactogenity index Ip is used in tests, which is calculated according to the formula Ip=Ck/Cv in which Ck and Cv designate neutrophiles in % relative to the initial level in the control and test group. If after 5 and 20 minutes Ip is less than 3, then the reactogenity probability is minimal [3].

Different methods for producing perfluorocarbon emulsions are known. Oil in water emulsions, which include perfluorocarbon emulsions and in which the perfluorocarbon basis is an oil phase, are produced at a high cost in energy. Comminution of the oil phase is implemented by ultrasound or mechanically.

Under the effects of ultrasound, a dispersion is implemented by frictional forces with intense local pressure change which has two causes. First, local compression and expansion alternate in the liquid with the passage of waves. Second, cavitation occurs, i.e. formation and collapse of cavities which are filled with the gases dissolved in water. The energy and the force of the ultrasound effect which are necessary in order to produce a sub-microemulsion are so large that, in addition to the dispersion, the C—F bond is broken. As a result, highly toxic concentrations of the F ions, approximately 3-5 mmol, appear in the aqueous phase of the emulsion. An emulsion with such a high concentration of $F^-$ ions cannot be used for blood replacement or for preserving perfusing organs. It is necessary to free it of the excess of $F^-$ ions by passage through an ion exchange resin. The second disadvantage of an emulsion dispersed by ultrasound is in an exceptionally high dispersion range because, with an average particle size of 0.1 μm, a large particle proportion can be found to be over 0.4 μm and under 0.01 μm in size.

A mechanical dispersion by shaking or intense agitation permits emulsions which are only coarsely dispersed to be obtained, with a particle size of over one millimetre which is not acceptable for biomedicinal application. In order to produce finely distributed emulsions forced passage of the substance of the disperse phase through fine holes into the dispersion medium under high pressure (extrusion) is used, as a result of which the liquid jet is broken up into droplets. The dispersion is effected by the pressure gradient and hydraulic frictional forces. The emulsions are normally produced in high pressure homogenisers. Stabilization of the obtained emulsions is achieved with the help of surface-active substances or emulsifiers. The stabilizing effect of these substances is explained by two causes: first by the reduction in excess surface energy between the phases or by the reduction of the surface tension and second by the formation of a structural, mechanical barrier (absorption layer) which ensures the stability of the particles and prevents contact or adhesion or agglomeration of the particles.

Amongst many surfactants, only a few fulfil the requirements for applicability to the production of preparations for intravenous injection (Table 4).

TABLE 4

Common surface-active substances for the production of perfluorocarbonemulsions

| Description | Structural formula | Basic parameters |
|---|---|---|
| Proxanol 268 (Pluronic F-68) | $HO(CH_2CH_2O)_x\text{—}(CH\text{—}CH_2O)_y\text{—}(CH_2CH_2O)_xOH$ with $CH_3$ branch | Synthetic blockcopolymer, mol.wt. ~13000 (P-268) and ~9000 (F-68), x = number of chain members of the ethylenepolyoxide block, y = number of chain members of the propylenepolyoxide block. Readily soluble. |
| phospholipids | $R_2\text{—}COOCH_2$<br>$R_1\text{—}COOCH$<br>$H_2C\text{—}O\text{—}P(O)(OH)\text{—}(O)\text{—}CH_2CH_2\text{—}R_3$ | Natural compound. $R_1$ and $R_2$ are different chains of the fatty acids. |
| (Egg yolk) lecithin | $R_3=N(CH_3)_3$ | Mol. wt. 760-870. Practically insoluble in water |

At the moment, mainly two emulsifiers are used to produce perfluorocarbon emulsions, namely Proxanol-268 (Pluronic F-68) and natural phospholipids (egg and soya phospholipids etc.).

The Proxanol structure does not correspond to the characteristic molecular properties of water-soluble surfactants which have a polar head (hydrophilic part) and a non-polar tail (hydrophobic part). In the case of Proxanol, the hydrophilic molecular character is determined by two polyoxideethylene chains, the hydrogen bonds being formed with $H_2O$ molecules. Methyl groups of polypropylenepolyoxide make lipophilic properties of its molecule a prerequisite. The ratio of the polyoxideethylene/polyoxidepolypropylene blocks for F-68 and P-268 is the same on average and is 80:20. The stabilizing effect of these emulsifiers is effected mainly by the steric effect of the protective film which is formed by the surface-active molecules around the fluorocarbon particles. The largest part of the surfactant molecules, in addition to the surfactants bonded in the absorption layer, thereby forms various micellar structures in the aqueous phase, including those which are free of fluorocarbon compounds. Between the surfactant molecules in the absorption layer and in the micells of the aqueous phase, a dynamic equilibrium is present which, on the one hand, is required for stabilisation of the absorption layer and, on the other hand, disturbs the density of the molecular packing of the surfactants in the absorption layer during long-term storage.

The phospholipids represent a mixture of compounds of natural origin, the general structure of which is indicated in Table 4. Phospholipids are water-insoluble and, at the same time, poorly lipophilic active substances with respect to different fluorocarbon compounds although they are partially dissolved by PFD and PFTPA in the double layer of the phosphatidyl choline particles. The cooperation of the phospholipids and fluorocarbon compounds in the aqueous phase has a double character. It is possible to include fluorocarbon compounds in the lamella structure of the phospholipids and/or to form monolayers of the phospholipids which are connected irreversibly to the particle surface. Non-homogeneous particles are possible in emulsions comprising fluorocarbon compounds and phospholipids, i.e. particles which are covered with a protective layer comprising phospholipids and free of phospholipids. This non-homogeneity can be attributed to production particularities and/or phospholipid excess relative to the fluorocarbon phase.

For finely distributed emulsions, the determining mechanism for reducing fineness (particle coarsening) is isothermic or molecular substance distillation of the disperse phase from small to larger particles by diffusion of the molecules of fluorocarbon compounds through a dispersion medium. This process is called "Ostwald ripening" of the emulsion or "recondensation". The driving force of this process is an increased pressure of saturated vapor over smaller particles in comparison to larger. In this case, an important parameter is also the level of solubility of fluorocarbon compounds in the aqueous medium. Prevention of recondensation can be of crucial importance for obtaining a resistant aggregate state of the perfluorocarbon emulsions, i.e. obtaining the fineness and individuality of the particles. The main routes to destabilization, namely molecular diffusion and a less significant flocculation and coagulation, are characteristic both of relatively dilute emulsions, in which the fluorocarbon phase is below 20% by volume, and of more highly concentrated emulsions in which the fluorocarbon phase is 50% by volume.

The stabilization routes of the perfluorocarbon emulsions are known. The basic principle of stabilization of colloid systems means prevention of their decomposition mechanisms. Addition of sugar and coemulsifiers with a negative charge (minority components of the phospholipids) in emulsions on a PFC/phospholipid basis prevents flocculation of the particles by changing the spatial interaction of the surfactant molecules in the absorption layer and also by increasing the electrostatic repulsion force between the particles.

Reducing the main decomposition process of the perfluorocarbon emulsions, which is caused by molecular diffusion, is achieved by addition of a second less water-soluble component (additional fluorocarbon compound) to the fluorocarbon basis which has a higher boiling temperature and slows down this process.

The principle of this stabilization is used in the development of the preparations Fluosol-DA, Perftoran and Oxygent. The compiled data are represented in the following Table 5 according to the composition and the physical-chemical properties of the mentioned preparations.

TABLE 5

Compiled data according to the composition of the preparations Fluosol-DA (Japan), Perftoran (Russia) and Oxygent (USA)/2/.

| | Concentration (% by vol./wt.) | | | | |
| --- | --- | --- | --- | --- | --- |
| | | | Oxygent | | |
| Ingredients | Fluosol-DA | Perftoran | AF0104 | AF0143 | AF0144 |
| Perfluorodecaline (PFD) | 14 | 13 | — | — | — |
| Perfluorotripropylamine (PFTPA) | 6 | — | — | — | — |
| Perfluoromethylcyclohexyl-piperidine (PFMHP) | — | 6.5 | — | — | — |
| Perfluorooctylbromide (PFOB) | — | — | 90 | 87 | 58 |
| Perfluorodecylbromide (PFDB) | — | — | — | 3 | 2 |
| Pluronic F-68 (Proxanol-268) | 2.72 | 4 | — | — | — |
| Phospholipids | 0.4 | — | 4 | 5.4 | 3.6 |
| Potassium oleate | 0.032 | — | — | — | — |
| Buffer substance | $CO_3^{-2}$ | $CO_3^{-2}$ | $PO_4^{-3}$ | $PO_4^{-3}$ | $PO_4^{-3}$ |
| Bivalent cations | + | + | — | — | — |

In the first two preparations, the fluorocarbon compounds perfluorotripropylamine and perfluoromethylcyclohexane-piperidine are added as supplements with a higher boiling temperature and less water-soluble to perfluorodecaline which has the greatest proportion of the oil phase. Water-soluble Pluronic F-68 with phospholipid supplement (Fluosol-DA) or its prototype Proxanol-268 (Perftoran) is used as emulsifier. They differ little from each other according to their physical-chemical properties. They belong to preparations of the first generation, the general disadvantage of which resides in the fact that, because of inadequate stability, they must be stored frozen. Perfluorodecylbromide, which has a higher boiling temperature and is less water-soluble, is added to the fluorocarbon basis of Oxygent (perfluorooctylbromide). The advantage of Oxygent which belongs to the second generation is determined by storage in the non-frozen state. Furthermore, perfluorooctylbromide, which is the fluorocarbon basis of the preparation is eliminated rapidly from the organism almost at the same rate as perfluorodecaline (corresponding to $t_{1/2}$~4 and 7 days).

Oxygent is a trade name of infusion media which are somewhat different with respect to composition.

The emulsifier not only contributes to lowering the superficial intermediate phase tension in the $H_2O$/PFC system which is required for fineness. A change in the emulsifier nature can influence the rate of the molecular diffusion. Fluorinated surfactants, which contain a fluorinated, hydrophobic and a non-fluorinated hydrophilic part in their molecule, are considered to be promising for the future. Great success in the synthesis of fluorinated surfactants for fluorocarbon compounds was achieved recently by French chemists [4]. The general structure of synthetic, fluorinated surfactants represents a combination of a perfluorinated chain and a polar head. A hydrocarbon chain is used as binding link of these elements. The polar head is selected from natural substances or derivatives thereof. Fluorinated surfactants, which contain alcohols or sugar derivatives as polar head, have a synergy with Pluronic F-68. The use of phospholipids, sugar phosphates or phosphatidyl choline in fluorinated surfactants as polar head increases the stability of the fluorocarbon emulsions which contain natural phospholipids as emulsifiers. A new class of mixed, fluorinated surfactants was proposed for stabilization [4]. The molecules of this class of fluorinated surfactants represent a block of two linear components, namely a hydrocarbon component and a perfluorinated component. The general formula of these compounds is as follows:

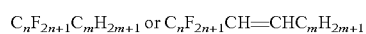

$$C_nF_{2n+1}C_mH_{2m+1} \text{ or } C_nF_{2n+1}CH=CHC_mH_{2m+1}$$

The inventors name these molecules "dowel" which means literally "spring" or "connection element".

The opinion prevails that molecules of fluorinated surfactants with a general, linear RH—RF structure play the role of a strengthening element, the hydrocarbon end of which enters into the lipid film which covers the perfluorocarbon particles and the other fluorinated end of which enters into the oil phase, i.e. that the RH-RF molecules improve the adhesion properties of the surfactant surface layer.

Now, perfluorodecaline and perfluorooctylbromide are the most accepted compounds for producing biomedicinal emulsions for the reason that they are eliminated rapidly from the organism in comparison to other fluorocarbon compounds.

Patents [5, 6] are known in which compositions of blood replacement agents are described, the fluorocarbon basis of which represent mixtures of two (perfluorodecaline/perfluoromethylcyclohexylpiperidine or perfluorodecaline/perfluorotributylamine or perfluorooctylbromide/perfluoromethylcyclohexylpiperidine), of three (perfluorooctylbromide/perfluorodecaline/perfluoromethylcyclohexylpiperidine or perfluorooctylbromide/perfluorodecaline/perfluorotributylamine) or even of four fluorocarbon compounds (perfluorooctylbromide/perfluorodecaline/perfluoromethylcyclohexylpiperidine/perfluorotributylamine) in a different ratio. These mixtures disperse by the water-soluble emulsifier Proxanol P-268. The use of this emulsifier does not make it possible to store the mentioned mixtures at positive temperatures. Furthermore, these emulsions, after thawing, have a limited storage duration at +4° (at most 1 month). That is their main disadvantage.

Emulsions with fluorinated surfactants are patent-protected. The known micro-emulsions containing fluorinated surfactants [7] have no practical application as infusion medium more for the reason that they are not sufficiently stable in vivo. Another composition of perflurocarbon emulsions, which are produced by mixed, fluorinated surfactants, is known, containing a fluorophilic part and a lipophilic part in the molecule [8]. These emulsions maintain in fact the mean particle average at positive temperatures but only within 3 months.

A patent [9] is known, in which a 10% fat emulsion of liposyn serves to produce emulsions as phospholipid source. Three groups of fluorocarbon compounds are patent-protected as fluorocarbon basis. Belonging to the first group are perfluorocycloalkanes or perfluoroalkylcycloalkanes (amongst those perfluorodecaline, perfluoromethyldecaline, perfluoroperhydrophenanthrene inter alia). The second group comprises perfluoroalkyl-saturated, heterocyclic compounds. The third group comprises perfluorinated, tertiary amines and perfluorotributylamine, perfluorotripropylamine inter alia. Perfluorooctylbromide also belongs to the applicable fluorocarbon compounds. However, it is still not possible to produce a stable perfluorodecaline emulsion with the help of the 10% liposyn. Its maximum storage duration is 25 days.

In a further patent [10], egg phospholipids are used for emulsion production. The proportion of the fluorocarbon phase changes within a large range of 10 to 50% by volume and that of the phospholipids from 0.5 to 7% by weight. As oil phase, only one of the PFCs from the broad class of compounds is selected and used in the patent, namely the perfluorohydrophenanthrene group with fluorine atoms from 1 to 24, perfluorodecaline, perfluorooctylbromide, perfluoromethyladamantane and perfluoroperhydrophenanthrene.

The main focus in both mentioned patents is on methods for preserving different organs and systems by the use of produced fluorocarbon emulsions. At the beginning of physiological tests, emulsions are mixed with crystalloid solutions and/or oncotic active substances (albumin, hydroxyethyl starch). The proposed emulsions in fact belong to emulsions of the second generation but have a substantial disadvantage. In both patents, examination results for emulsion stability, i.e. maintaining the particle size with long-term storage (over a month), is not indicated. The two just mentioned patents [9, 10] are regarded here as prototypes.

The closest prototype to the emulsion according to this invention is the emulsion mentioned under [11]. This emulsion, regarded as prototype, belongs to the second generation and contains a rapidly eliminated fluorocarbon compound in the quantity of 40 to 50% by volume and a perfluorinated supplement of a higher-boiling compound of 5 to 10% by volume. As a rapidly eliminated fluorocarbon compound, perfluorodecaline or perfluorooctylbromide (main component) is used and, as supplement, perfluoromethylcyclohexylpiperidine. The emulsifier is egg or soya phospholipid.

The perfluorocyclohexylpiperidine stabilises the emulsion, reduces the rate of molecular diffusion (recondensation) of the main components (perfluorodecaline or perfluorooctylbromide) and is used to produce emulsions of a different composition, namely Perftoran. The main disadvantage of the emulsion known from patent [11] is a relatively large particle average above 0.2 μm.

SUMMARY OF THE INVENTION

One object of this invention resides in increasing the stability of the emulsion and in improving the quality of the emulsion, i.e. in obtaining biocompatibility with the biological medium (blood, plasma or serum) with a storage of at least 6-12 months in the non-frozen state.

The emulsion according to this invention for medicinal purposes contains rapidly eliminated perfluorodecaline or perfluorooctylbromide and also a perfluorinated supplement and a phospholipid. This emulsion is characterized in that a composition of mixed perfluorodecaline and perfluorooctylbromide is used as rapidly eliminated component, and the perfluorinated supplement represents a mixture of perfluorinated tertiary amines, and the phospholipids are used as a dispersion in the water-salt medium.

The emulsion is further characterized in that the total concentration of fluorocarbon compounds is in the range of 2 to 40% by volume.

The emulsion is further characterized in that the composition contains the rapidly eliminated perfluorodecaline and perfluorooctylbromide in a ratio of 10:1 to 1:10, in that the perfluorinated supplement is 1% to 50% of the total content of the fluorocarbon compounds and contains cis- and trans-isomers of perfluoro-1-propyl-3,4-dimethylpyrrolidone and perfluoro-1-propyl-4-methylpiperidine and also additional perfluoro-N-methylcyclohexylpiperidine and coproducts thereof.

The emulsion is further characterized in that it contains a dispersion of the egg and soya phospholipids or a mixture of these lipids in the water-salt medium in the concentration of 0.2 to 5% by weight.

The emulsion is further characterized in that the phospholipid dispersion in the water-salt medium contains an adjuvant of 1 to 15% of the total content of the phospholipids. Vegetable oil is used as adjuvant and in fact soya, sunflower seed or ricinus oil or a mixture of these oils in the effective ratio as a twofold or threefold mixture.

The emulsion is further characterized in that the water-salt medium contains sodium salts and potassium salts of chlorides and phosphates and also the monosaccharide mannitol in the injection water and the concentration of the components in the water-salt medium has an osmotic pressure in the range of 100 to 350 mosmol/l.

The emulsion is further characterized in that the mean particle size does not exceed 0.2 μm and is in the range of 0.06-0.2 μm.

The production method of the emulsion according to this invention by homogenization is characterized in that the method contains a plurality of steps which include a phospholipid dispersion in the water-salt medium, homogenization in the phospholipid dispersion, heat sterilization of the produced emulsion and subsequent storage of at least 6 months in the non-frozen state at a temperature of +4° C.

The production method according to the invention is further characterised in that the phospholipid dispersion in the water-salt medium is produced by homogenisation at a high pressure of at least 100 atm and with a subsequent sterilisation.

The production method according to the invention is further characterized in that the fluorocarbon compounds in the phospholipid dispersion are homogenized at a pressure of 300 to 650 atm.

The production method according to this invention is further characterized in that the phospholipid dispersion and emulsion are sterilized at a temperature of 100° C.

DETAILED DESCRIPTION OF THE INVENTION

As is indicated above, the object of the invention resides in increasing the emulsion stability and improving the emulsion quality, i.e. in obtaining biocompatibility in the biological medium (blood, plasma or serum) with storage of 6-12 months in the non-frozen state. The term biocompatibility includes different variables and should be made precise relative to the emulsion. In the above-mentioned patents [8-11], there is understood by biocompatibility a relatively high elimination rate of the chosen PFCs, the ability to preserve the tissues and organs through which the emulsion is perfused and a comparatively low toxicity for animals (at least 2 volumes of throughflowing blood). These ideas are not mutually exclusive but do not reflect the first step, namely the cooperation of the particles with plasma and blood in the bloodstream. In this invention, the biocompatibility begins with the level of significance of the cooperation (reaction) of the emulsion with the biological medium (blood, plasma or serum). The results of this cooperation can be evaluated not only in vivo but also above all in tests in vitro according to the stabilization level of the emulsion with the influence of a series of factors which simulate damage to the absorption layer during storage and penetration of the emulsion into the bloodstream.

The quality and stability of the emulsions is normally characterized on the basis of particle size and in fact the mean particle average should not exceed 0.2-0.3 µm. Such an approach is not adequate for biomedicinal, dispersed preparations for intravenous injection. This is based on the fact that the fluorocarbon particles cooperate as foreign material with proteins and molecules of other compounds found in the plasma and also with blood cells during penetration into the bloodstream. The general character of the cooperation depends upon the properties of the particle surface. The functional activity (gas transport function) of the emulsions depends substantially upon the compatibility of the surface of the emulsified particles with blood and plasma since a reaction cascade is initiated for example during system activation of the complement on the foreign surface, said reaction cascade being caused by vascular spasm and interference in the regional blood flow. It should also be noticed that the emulsion stability in vitro is greatly affected by the properties of the absorption layer of surfactants around the particles (strength, topography of the surface etc.). In the sense of what has just been mentioned, the problem of emulsion stability can be resolved only by normal chemical colloid methods of particle examination without evaluation of the structural particularities. Development in this respect of simple methods and approaches which can provide information about the particle size and totality of the particle structure is extremely topical. The term structure itself is thereby intended to be made precise with respect to emulsions.

Progress in the examination of emulsion stability in vitro and in vivo is connected to the broadening and extension of the term structure and also upon the development of examination methods of the structure. The term stability of a preparation or of a substance is determined by the stability of the properties of the diverse preparation or of this substance. The parameters determining the properties of the emulsion do not adequately characterize the stability of the emulsion. In tests on this side, ideas about the stability of the emulsions taking into account peculiarities of the structure of the emulsion are broadened.

The stability of the carbon emulsions is normally evaluated after alteration of the particle size of the emulsion during storage. This purely chemical colloid approach is inadequate. For emulsions which represent the basis of preparations and are intended to be used for intravenous injections, information about the emulsion stability is not only of great significance in in vitro tests but also the possibility of predicting the emulsion stability when flowing through the bloodstream. This information can be obtained if ideas about the emulsion structure can be fixed clearly. The particles of the emulsions have the shape of a two-layer ball, in the middle of which there is a PFC (particle core) and on the surface of which there is an emulsifier layer (shell) [12]. The shell thickness of the emulsifier is low and is 5-10% of the particle diameter. The behavior of the emulsions in the bloodstream (cooperation with plasma proteins and blood cells, elimination rate etc.) and the stability during long-term storage depend greatly however upon the strength and the state of the surface-active substance around the particles. For this reason, it is necessary to obtain information at the same time about the particle size and the structural change in the media to be examined in the case of those or other effects.

For the theoretical description and analysis of structural change in emulsions as the basis of infusion media, the following ideas should be emphasised [13]:

1) The "total structure" of the emulsions and their change is characterized by the mean particle average and the distribution according to the particle size.

2) The "microstructure" is characterized by the emulsifier state in the shell and the degree of cooperation of the emulsifier with PFCs, the mutual position of the surfactant molecules, their arrangement, packing density, degree of oxidation and the phase state of the structured molecules.

To date, all researchers have restricted themselves to the analysis of a "general structure" which is totally inadequate because the emulsion stability, biocompatibility and in particular the particle surface properties and the absorption capacity of the particles are determined by the microstructure.

The emulsions according to this invention were compared with the prototype and above all examined for parameters which characterize the change in the general structure with different storage times of produced emulsions.

Secondly, the effect of destructive factors on the emulsion was simulated under conditions which allow the microstructure state of the emulsion to be evaluated. Namely a "stress effect" in the form of a dilution with water was used and a specific change in the parameters in comparison to the native emulsion was undertaken. The water dilution of the emulsions disturbs the set equilibrium between the absorption layer of the surfactants (shell) and the surfactant molecules in the dispersion medium. For this reason, it has a specific prognostic meaningfulness with respect to maintaining the stability of the metastable system (fluorocarbon emulsion) or the decomposition thereof.

Furthermore, the change in microstructure and the compatibility of the emulsions during contact with blood serum as system model was examined (examination of the biocompatibility of the emulsion in in vitro tests). The cooperation of two heterogeneous disperse systems, blood serum and fluorocarbon emulsion, characterizes the change in surface particle properties during penetration into the bloodstream and the microstructure change in the emulsion during storage. The change in the general structure and the microstructure was examined at equal periods of time in the course of 12 months.

In order to detect the changes in the mentioned state parameters during storage, methods and approaches were needed which would not have introduced additional disturbances into the system to be examined during measurements. As such, optical testing methods were selected, tested and developed.

In order to evaluate the general structure, a turbidimetric method or turbidity spectrum method [14] was chosen by the inventors. This method was used also for evaluating the particle size distribution in the emulsions to be examined after centrifugation and fractionation. The change in microstructure of the emulsion or of the particle surface properties which were caused by change in the interrelation of the surfactant molecules in the absorption layer around the fluorocarbon compounds were evaluated with an indirect method in order to find the interaction index ($K_r$) of the emulsion to be examined with blood serum relative to the physiological common salt solution: the relative turbidity $K_r=\tau_1/\tau_2$, $\tau_1$ and $\tau_2$ meaning the turbidity of the mixtures of serum/emulsion and serum/physiological common salt solution with a corresponding change in the ratio of components of the mixture [15]. In addition, calculated and experimental τ-values were compared in order to confirm the natural constancy of emulsified particles: $\tau_{calculated}=\Sigma N_i \Box \tau_i$ ($\Sigma N_i=1$), $\tau_i$ and $N_i$ meaning the turbidity or the proportion of the eliminated fraction and $\tau_{experiment}$ the turbidity of the same emulsion sample before fractionation.

I. Concrete Compositions of the Emulsion According to this Invention are Indicated in the Following.

Composition 1

The emulsion contains 40% by volume of a fluorocarbon phase ($C_v$) comprising perfluorodecaline and perfluorooctyl-bromide in the ratio 1:1 with a perfluorinated supplement as mixture of perfluorotripropylamine and its coproducts: cis- and trans-isomers of perfluoro-1-propyl-3,4-dimethylpyrrolidone and perfluoro-1-propyl-4-methylpiperidine in a quantity of 50% of the total content of fluorocarbon compounds, stabilized in the emulsified state with 5% phospholipid dispersion, which contains egg phospholipid and ricinus oil as adjuvant, the concentration of which is 15% of the total content of the egg phospholipid, in the water-salt medium of the following composition: 2 mmol (115 mg/l) sodium chloride, 2 mmol once-substituted potassium dihydrogen phosphate (310 mg water-free salt/l), 7.5 mmol twice-substituted sodium dihydrogen phosphate (460 mg water-free salt/l), 318 mmol mannite (58 g mannitol/l) in injection water. The osmotic pressure was 310 mosmol/l. The mean average diameter of the emulsion particles was 0.195 μm.

Composition 2

The emulsion according to composition 1 was characterized in that it contained 20% by volume of a fluorocarbon phase ($C_v$) comprising perfluorodecaline and perfluorooctyl-bromide in the ratio 10:1 with a supplement as mixture of perfluorotripropylamine and its coproducts: cis- and trans-isomers of perfluoro-1-propyl-3,4-dimethylpyrrolidone and perfluoro-1-propyl-4-methylpiperidine, with additional perfluoro-N-methylcyclohexylpiperidine in a quantity of 25% of the total content of the fluorocarbon compounds, stabilized in the emulsified state with 25% phospholipid dispersion, which contains soya phospholipid and soya oil as adjuvant, the concentration of which is 10% of the total content of the egg phospholipid, in the water-salt medium of the following composition: 2 mmol once-substituted, sodium dihydrogen phosphate (276 mg water-free salt/l), 7.5 mmol twice-substituted, sodium dihydrogen phosphate (460 mg water-free salt/l), 278 mmol mannite (50 g mannitol/l) in injection water. The osmotic pressure was 270 mosmol/l. The mean average diameter of the emulsion particles was 0.1 μm.

Composition 3

The emulsion according to composition 1 was characterized in that it contained 15% by volume of a fluorocarbon phase ($C_v$) comprising perfluorodecaline and perfluorooctyl-bromide in the ratio 1:10 with a supplement as mixture of perfluorotripropylamine and its coproducts: cis- and trans-isomers of perfluoro-1-propyl-3,4-dimethylpyrrolidone and perfluoro-1-propyl-4-methylpiperidine, with additional perfluoro-N-methylcyclohexylpiperidine in a quantity of 5% of the total content of the fluorocarbon compounds, stabilized in the emulsified state with 2% phospholipid dispersion, which contains soya and egg phospholipid and sunflower seed oil as adjuvant, the concentration of which is 5% of the total content of phospholipids, in the water-salt medium of the following composition: 1 mmol once-substituted, sodium dihydrogen phosphate (138 mg water-free salt/l), 3.7 mmol twice-substituted, sodium dihydrogen phosphate (230 mg water-free salt/l), 100 mmol mannite (18 g mannitol/l) in injection water. The osmotic pressure was 105 mosmol/l. The mean average diameter of the emulsion particles was 0.08 μm.

Composition 4

The emulsion according to composition 1 was characterized in that it contained 10% by volume of a fluorocarbon phase ($C_v$) comprising perfluorodecaline and perfluorooctyl-bromide in the ratio 2:1 with a supplement as mixture of perfluorotripropylamine and its coproducts: cis- and trans-isomers of perfluoro-1-propyl-3,4-dimethylpyrrolidone and perfluoro-1-propyl-4-methylpiperidine, with additional perfluoro-N-methylcyclohexylpiperidine in a quantity of 0.2% of the total content of the fluorocarbon compounds, stabilized in the emulsified state with 2% phospholipid dispersion, which contains egg phospholipid and sunflower seed and soya oil as adjuvant, the concentration of which is 2% of the total content of the egg phospholipids, in the water-salt medium of the following composition: 1 mmol once-substituted, sodium dihydrogen phosphate (138 mg water-free salt/l), 3.7 mmol twice-substituted, sodium dihydrogen phosphate (230 mg water-free salt/l), 90 mmol mannite (13 g mannitol/l) in injection water. The osmotic pressure was 100 mosmol/l. The mean average diameter of the emulsion particles was 0.07 μm.

Composition 5

The emulsion according to composition 1 was characterized in that it contained 2% by volume of a fluorocarbon phase ($C_v$) comprising perfluorodecaline and perfluorooctyl-bromide in the ratio 1:2 with a supplement as mixture of perfluorotripropylamine and its coproducts: cis- and trans-isomers of perfluoro-1-propyl-3,4-dimethylpyrrolidone and perfluoro-1-propyl-4-methylpiperidine, with additional perfluoro-N-methylcyclohexylpiperidine in a quantity of 10% of the total content of the fluorocarbon compounds, stabilized in the emulsified state with 0.2% phospholipid dispersion, which contains soya phospholipid and soya and ricinus oil as adjuvant, the concentration of which is 5% of the total content of the soya phospholipids, in the water-salt medium of the following composition: 2 mmol sodium chloride (115 mg water-free salt/l), 2 mmol once-substituted sodium dihydrogen phosphate (276 mg water-free salt/l), 7.5 mmol twice-substituted sodium dihydrogen phosphate (460 mg water-free salt/l), 318 mmol mannite (58 g mannitol/l) in injection water. The osmotic pressure was 350 mosmol/l. The mean average diameter of the emulsion particles was 0.06 μm.

Composition 6

The emulsion according to composition 1 was characterized in that it contained 10% by volume of a fluorocarbon phase ($C_v$) comprising perfluorodecaline and perfluorooctyl-bromide in the ratio 4:1 with a supplement as mixture of perfluorotripropylamine and its coproducts: cis- and trans-isomers of perfluoro-1-propyl-3,4-dimethylpyrrolidone and perfluoro-1-propyl-4-methylpiperidine, in a quantity of 4% of the total content of the fluorocarbon compounds, stabilized in the emulsified state with 2% phospholipid dispersion, which contains soya phospholipid and sunflower seed, soya and ricinus oil as adjuvant, the concentration of which is 4% of the total content of phospholipid, in the water-salt medium of the following composition: 2 mmol once-substituted, sodium dihydrogen phosphate (276 mg water-free salt/l), 7.5 mmol twice-substituted sodium dihydrogen phosphate (460 mg water-free salt/l), 200 mmol mannite (36 g mannitol/l) in injection water. The osmotic pressure was 225 mosmol/l. The mean average diameter of the emulsion particles was 0.09 µm.

In the following Table 6, compositions of the emulsions according to this invention are represented according to the compositions 1-6.

a drying chamber at 110° C. Thereafter, 0.138 g water-free, once-substituted sodium dihydrogen phosphate, 0.523 g water-free, twice-substituted sodium dihydrogen phosphate and 50.0 g mannite were dissolved in 1 l apyrogenic water in a laminar device under aseptic conditions. The obtained water-salt solution was conducted through a sterile filter from the Millipor Company with a pore size of 0.4 µm.

TABLE 6

Compositions 1-6 of the fluorocarbon emulsions

| No. | $C_v$ % by vol. PFD/PFOB | Fluorocarbon supplement Relative content | Dispersion Phospholipids % by wt. | Adjuvant relative content | Osmo-molarity | Particle size | Aqueous phase composition in mmol |
|---|---|---|---|---|---|---|---|
| 1 | 40% by vol. 1:1 | Fl. 50% | Egg-P 5% | Ricinus oil 15% | 310 | 0.195 µm | 2 KCl 2 NaH$_2$P 7.5 Na$_2$HP 318 mannite |
| 2 | 20% by vol. 10:1 | Fl. perfluoromethylcyclo-hexylpiperidine 25% | Soya-P 2.5% | Soya oil 10% | 270 | 0.10 µm | 2 NaH$_2$P 7.5 Na$_2$HP 278 mannite |
| 3 | 25% by vol. 1:10 | Fl. Perfluoromethylcyclo-hexylpiperidine 5% | Egg and soya phospholipid 2% | Sunflower seed oil 10% | 110 | 0.08 µm | 1 NaH$_2$P 3.7 Na$_2$HP 100 mannite |
| 4 | 10% by vol. 2:1 | Fl. perfluoromethylcyclo-hexylpiperidine 0.2% | Egg phospholipid 2% | Sunflower seed and ricinus oil 2% | 100 | 0.07 µm | 1 NaH$_2$P 3.7 Na$_2$HP 95 mannite |
| 5 | 2% by vol. 1:2 | Fl. perfluoromethylcyclo-hexylpiperidine 10% | Soya phospholipid 0.2% | Soya and ricinus oil 5% | 350 | 0.06 µm | 2 NaCl 2 NaH$_2$P 7.5 Na$_2$HP 318 mannite |
| 6 | 10% by vol. 4:1 | Fl. 4% | Soya phospholipid 2% | Sunflower seed, soya and ricinus oil 2% | 225 | 0.09 µm | 2 NaH$_2$P 7.5 Na$_2$HP 200 mannite |

II. Concrete Embodiments for the Production Method of the Composition of the Emulsions According to this Invention and the Physical-Chemical Parameters of the Emulsions are Indicated in the Examples.

EXAMPLE 1

The Emulsion was Produced Under Aseptic Conditions 1.1 For production, 1 l emulsion was prepared with 10% by volume of PFC to a 1% phospholipid dispersion.

1.2 First step dispersion preparation: a sterile, round flask was filled with 100 ml 10% alcohol solution of egg phospholipid. The alcohol was distilled in a rotary evaporator. 1 g ricinus oil (adjuvant concentration 10% of egg phospholipid content) and 900 ml water-salt solution were added.

1.3 Apyrogenic water was used to prepare the water-salt solution. A powder comprising once-substituted sodium dihydrogen phosphate, twice-substituted sodium dihydrogen phosphate and crystalline mannite were dried for 2 hours in 1.4 A mixture of vegetable oil and the water-salt solution was agitated mechanically in the flask until a homogeneous suspension of a milky-yellow colour was obtained. The obtained phospholipid suspension was added to a sterile container of a high pressure homogenizer.

1.5 The homogenizer was sterilized in advance with superheated water vapor and 500 ml alcohol and washed with 500 ml apyrogenic hot water.

1.6 The phospholipid suspension was conducted through the homogenizer four times at a pressure of 100 atm until a semi-transparent, homogeneous liquid was obtained. The obtained dispersion was decanted into glass vessels. The glass vessels were treated for 2-4 minutes with sterile, inert gas (nitrogen, argon or a mixture of nitrogen and carbon dioxide).

1.7 The glass vessels were sealed with rubber seals and covered with aluminium caps. Thereafter, the vessels were heat-sterilized for 1 hour at 100° C. The vessels were stored at room temperature until the next production step.

1.8 PFCs were treated in the next step. 72 ml PFD were mixed with 8 ml PFOB. 20 ml perfluorotripropylamine were added to 80 ml of this composition. The obtained composition comprising PFD and PFOB with a supplement of fluorocarbon was mixed with the same volume of medicinal alcohol. The perfluorocarbon phase was separated from the alcohol which is heavier by means of a separating funnel. The separated mixture was mixed with a threefold volume of apyrogenic water, shaken and separated in the separating funnel (specific fluorocarbon weight exceeds the specific water weight virtually twofold).

1.9 Thereafter, the emulsion was produced. 900 ml phospholipid dispersion and 100 ml treated fluorocarbon mixture (composition comprising PFD/PFOB=9/1+PFTPA−20%) were added to the homogenizer. The contents were agitated mechanically and dispersed at a pressure of 500 atm, the total volume flowing through the chamber eight times until a semi-transparent, yellowish liquid with an opalescent color, the submicron emulsion, was obtained. The emulsion was decanted into glass vessels with respectively 100 ml. The glass vessels were plugged with rubber seals and covered with aluminum caps.

1.10 The emulsion in vessels was heat-sterilized for 1 hour at 100° C., then cooled and stored for one year at 4° C.

The obtained emulsion had the following composition: fluorocarbon phase ($C_v$) 10% by volume, ratio of PFD to PFOB 9/1, relative content of PFTPA in the fluorocarbon mixture 20%, concentration of egg phospholipid 1% by weight, ricinus oil concentration 0.1% (relative ricinus oil content in suspension as adjuvant 10% of the total content of the egg phospholipid). Lot No. 1.

The viscosity of the lot was measured by means of a viscosity meter model ВПЖ-2, and was 0.953 cP (centipoise). In comparison to Perftoran with the same content of fluorocarbon phase, the viscosity was 2.5 cP (centipoises).

Example 2

The emulsion was produced in the same composition and as in example 1. A mixture of soya and ricinus oil in the ratio of 1:1 was selected as adjuvant. The emulsion had the following composition: $C_v$ 10% by volume, PFD/PFOB 9:1, relative content of PFTPA 20%, egg phospholipid concentration 1% by weight, relative adjuvant content (soya/ricinus oil 1:1) 10%. Lot No. 2.

Example 3

The emulsion was produced as in example 1 in the same composition but in a volume of 800 ml with a fluorocarbon content of 20% by volume. 200 ml 10% alcohol solution of soya phospholipids were added to round flasks. The alcohol was distilled in the rotary evaporator. 3 g adjuvant (soya and ricinus oil in the ratio 1:2, adjuvant concentration 15% of the egg phospholipids) were added. The water-salt solution contained 0.276 g water-free, once-substituted sodium dihydrogen phosphate, 1.046 g water-free, twice-substituted sodium dihydrogen phosphate and 10.0 g mannite. 1 l water-salt solution was added to the flask with the adjuvant, shaken and dispersed in the homogenizer, decanted into glass vessels and sterilized as in example 1. The fluorocarbon phase was prepared. 40 ml PFOB were added to 160 ml PFD. From this quantity, 160 ml of the composition were taken and mixed with 40 ml PFTPA. After cleaning, 200 ml obtained perfluorocarbon mixture were added in drops to the homogenizer with 800 ml dispersion of soya phospholipid. The obtained emulsion was decanted and sterilized.

The emulsion had the following composition: $C_v$=20% by volume, ratio of PFD to PFOB 8:2, relative content of PFTPA 20%, soya phospholipid concentration 2% by weight, relative adjuvant content (soya/ricinus oil 1:2) 15%. Lot No. 3.

Example 4

The emulsion was produced as in example 1 but with a ratio of PFD to PFOB of 8:2. 30 ml PFMHP were added to 170 ml of the composition, mixed by shaking, cleaned as per normal and added in drops into a homogenizer with 800 ml dispersion comprising soya phospholipid (obtained as in example 3) and the same adjuvant: soya and ricinus oil in the ratio 1:2 in a quantity of 15% of the soya phospholipid content. The emulsion was dispersed at a pressure of 400 atm.

The emulsion had the following composition: $C_v$=20% by volume, PFD/PFOB ratio 8:2, relative content of PFMP 15%, soya phospholipid concentration 2% by weight, relative adjuvant content (soya/ricinus oil 1:2) 15%. Lot No. 4.

Example 5

The emulsion was produced as in example 1 only with the addition of a different quantity of the egg phospholipid. 50 ml egg phospholipid were added to round flasks. The alcohol was distilled in the rotary evaporator. 0.6 g sunflower seed oil and 0.5 g common salt solution were added, mixed by shaking and homogenized at a pressure of 150 atm. The composition of PFD/PFOB in the ratio 5:5 was prepared by mixing with 25 ml PFD and 25 ml PFOB. 49.5 ml mixture were mixed with 0.5 ml PFTPA. 50 ml of the mixture were added, after cleaning, to a homogenizer with 0.95 l suspension of the egg phospholipid. The homogenization of the presuspension was implemented at a pressure of 350 atm. Decanting and sterilization of the finely distributed emulsion was implemented according to the prescribed rules.

The emulsion had the following composition: $C_v$=5% by volume, PFD/PFOB ratio 5:5, relative content PFIPA 1%, egg phospholipid concentration 0.5% by weight, relative adjuvant content sunflower seed oil, 12%. Lot No. 5.

Example 6

50 ml 10% alcohol solution of soya phospholipid were added to round flasks. The alcohol was distilled according to the above-described method. 0.6 g soya oil and 950 ml salt solution were added. After mixing, the dispersion was produced in a homogenizer at a pressure of 180 atm. After the sterilization, the dispersion was used to produce the emulsion. A composition of PFD and PFOB (in the ratio 5:5) was produced by mixing with 25 ml PFD and 25 ml PFOB. 0.5 ml PFMHP was added to 49.5 ml of this composition. After cleaning with 50 ml alcohol, the mixture was processed in the homogenizer with 950 ml soya phospholipid dispersion. The homogenization was implemented in two stages, as mentioned above, in the first stage at a pressure of 200 atm and in the second stage at a pressure of 500 atm.

The obtained emulsion had the following composition: $C_v$=5% by volume, PFD/PFOB ratio 5:5, relative content of PFMHP 1%, soya phospholipid concentration 0.5% by weight, relative adjuvant content (soya oil) 12%. Lot No. 6.

Example 7

A suspension was prepared with a concentration of soya phospholipids of 0.2% by weight. In addition, 20 ml alcohol solution of the soya phospholipid were added to a rotary evaporator. The alcohol was distilled. The mixture of soya and sunflower seed oil in the ratio 1:1 as adjuvant was added thereto. The dispersing and sterilization with the addition of 980 ml common salt solution was implemented as in example 6.

The composition of PFD/PFOB was prepared by mixing 4 ml PFD and 16 ml PFOB (in the ratio 2:8). 1 ml PFMHP was added to 19 ml of the mixture. 20 ml of the obtained mixture of the three components was homogenized with 980 ml suspension. The homogenization was implemented as in the example above. The sterilization and the decanting were implemented according to standard methods.

The obtained emulsion had the following composition: $C_v$=2% by volume, PFD/PFOB ratio 2:8, relative content of PFMHP 5%, soya phospholipid concentration 0.2% by weight, relative adjuvant content (soya/sunflower seed oil 1:1) 1%. Lot No. 7.

Example 8

In order to produce the emulsion, 40% by weight suspension of the egg phospholipid were prepared with a concentration of 5% by weight. 500 ml alcohol solution of the egg phospholipid were added in addition to a flask. The alcohol was distilled. 2.5 g ricinus oil as adjuvant and 600 ml common salt solution were added thereto. After mixing, the dispersing was implemented in a homogenizer at a pressure of 200 atm until a homogeneous medium of a yellowish-white color was obtained. The sterilization was implemented as indicated above.

The composition was prepared by mixing with 4 ml PFD and 360 ml PFOB (in the ratio 1:9). 40 ml PFMHP were added to 360 ml of the mixture. 400 ml of the obtained mixture of the three components were homogenized in two stages with 600 ml suspension of the egg phospholipid, in the first stage at a pressure of 250 atm and in the second stage at a pressure of 600 atm. The sterilization and decanting were implemented according to standard methods.

The emulsion had the following composition: $C_v$=40% by volume, PFD/PFOB ratio 1:9, relative content of PFMHP 10%, egg phospholipid concentration 5% by weight, relative adjuvant content (ricinus oil) 5%. Lot No. 8.

Example 9

A fluorocarbon phase was mixed from 40 ml PFD and 360 PFOB. 80 ml were added to 320 ml of the mixture, and in fact 40 ml PFMHP and 40 ml of an organic liquid. The emulsifier suspension comprised 4.2% by weight egg phospholipid, 4.2% by weight soya phospholipid and 4.2 g adjuvant comprising ricinus and sunflower seed oil in the ratio 9:1, i.e. 5% of the total content of the egg phospholipid.

In order to produce the emulsion, 600 ml suspension with 400 ml of the mixture of three components were added to a homogenizer. The homogenization, decanting and sterilization were implemented as in the above example.

The emulsion had the following composition: $C_v$=40% by volume, PFD/PFOB ratio 1:9, relative content PFMHP and organic liquid 20%, phospholipid concentration (egg and soya phospholipid 1:1) 5% by weight, relative adjuvant content (ricinus and sunflower seed oil 9:1) 0.25%. Lot No. 9.

Compositions of all the lots are indicated in Table 7.

In Table 8, examination results of the mean particle size are indicated for native (not diluted) and water-diluted emulsions for different storage times.

TABLE 7

Composition of the obtained emulsions according to lots (examples 1-9)

| Lot no. | $C_v$ % by vol. | Ratio PFD/PFOB | Supplement relative content | Phospholipids % by wt. | Adjuvant | Adjuvant relative content in % |
|---|---|---|---|---|---|---|
| 1 | 10 | 9:1 | Fl. 20% | Egg phospholipids 1% | Ricinus | 10 |
| 2 | 10 | 9:1 | Fl. 20% | Egg phospholipids 1% | Ricinus/soya 1:1 | 10 |
| 3 | 20 | 8:2 | Fl. 20% | Soya phospholipids 2% | Ricinus/soya 2:1 | 15 |
| 4 | 20 | 8:2 | PFMHP 15% | Soya phospholipids 2% | Ricinus/soya 2:1 | 15 |
| 5 | 5 | 5:5 | Fl. 1% | Egg phospholipids 0.5% | Sunflower seed | 12 |
| 6 | 5 | 5:5 | PFMHP 1% | Soya phospholipids 0.5% | Soya oil | 12 |
| 7 | 2 | 2:8 | PFMHP 5% | Soya phospholipids 0.2% | Soya/sunflower seed 1:1 | 1 |
| 8 | 40 | 1:9 | PFMHP 10% | Egg phospholipids 5% | Ricinus/sunflower seed 9:1 | 5 |
| 9 | 40 | 1:9 | Fl. 10% PFMHP 10% | Egg phospholipids 2.5% soya phospholipids 2.5% | Ricinus/sunflower seed 9:1 | 5 |

TABLE 8

Wavelength exponent and mean particle size for native and water-diluted fluorocarbon emulsions from examples 1, 3, 4, 5, 8 and 9

| | | n | | a, µm | |
|---|---|---|---|---|---|
| Lot no. | Storage months | native | diluted 1:2 | native | diluted 1:2 |
| 1-01 | 0 | 3.40 | 3.20 | 0.114 | 0.13 |
| | 1 | 3.33 | 3.33 | 0.119 | 0.119 |
| | 3 | 3.23 | 3.20 | 0.128 | 0.13 |
| | 6 | 3.27 | 3.23 | 0.124 | 0.128 |
| | 9 | 3.13 | 3.30 | 0.136 | 0.121 |
| | 12 | 3.05 | 3.14 | 0.143 | 0.135 |

TABLE 8-continued

Wavelength exponent and mean particle size for native and water-diluted fluorocarbon emulsions from examples 1, 3, 4, 5, 8 and 9

| | | n | | a, µm | |
|---|---|---|---|---|---|
| Lot no. | Storage months | native | diluted 1:2 | native | diluted 1:2 |
| 1-03 | 0 | 3.27 | 3.33 | 0.125 | 0.119 |
| | 1 | 3.33 | 3.33 | 0.119 | 0.119 |
| | 3 | 3.13 | 3.20 | 0.136 | 0.13 |
| | 6 | 3.20 | 3.27 | 0.130 | 0.124 |
| | 12 | 3.20 | 3.13 | 0.130 | 0.136 |
| 1-04 | 0 | 3.20 | 3.13 | 0.13 | 0.136 |
| | 1 | 3.17 | 3.0 | 0.132 | 0.148 |
| | 3 | 2.87 | 3.10 | 0.165 | 0.14 |
| | 6 | 3.07 | 3.10 | 0.141 | 0.138 |
| | 9 | 3.10 | 3.07 | 0.138 | 0.141 |
| | 12 | 2.94 | 2.85 | 0.155 | 0.17 |
| 1-05 | 0 | 3.20 | 3.27 | 0.13 | 0.124 |
| | 1 | 3.13 | 3.07 | 0.136 | 0.14 |
| | 3 | 3.03 | 3.07 | 0.146 | 0.14 |
| | 6 | 3.07 | 3.03 | 0.141 | 0.145 |
| | 12 | 2.97 | 3.10 | 0.148 | 0.138 |
| 1-08 | 0 | 3.33 | 3.27 | 0.113 | 0.124 |
| | 1 | 3.23 | 3.26 | 0.128 | 0.126 |
| | 3 | 3.10 | 3.20 | 0.139 | 0.13 |
| | 6 | 3.03 | 3.11 | 0.14 | 0.14 |
| | 9 | 2.88 | 3.10 | 0.164 | 0.138 |
| | 12 | 2.87 | 2.9 | 0.165 | 0.160 |
| 1-09 | 0 | 3.16 | 3.20 | 0.134 | 0.13 |
| | 1 | 3.0 | 3.13 | 0.148 | 0.137 |
| | 3 | 3.0 | 3.07 | 0.148 | 0.141 |
| | 6 | 2.86 | 3.02 | 0.182 | 0.157 |
| | 12 | 2.7 | 3.07 | 0.195 | 0.14 |

The value n was calculated according to the method of least squares. The mean error square in the determination of n is 0.01-0.03. Hence the error in the determination of n=0.3-1%. The parameter n is a characteristic function of the turbidity spectrum method and is calculated according to at least 3-5 points. For finely distributed emulsions, n is connected unequivocally with the mean particle size a [14].

According to the obtained results, the average parameters n and a practically do not change in the case of 12 months storage. The water dilution as stress effect affected the particle size little. A slight increase in the values a was observed for emulsions with soya phospholipids at later times of 9-12 months. The range of change for the wavelength exponent for all lots of the fluorocarbon emulsions with phospholipid dispersion with storage up to one year was between 3.4 and 2.7. This corresponded to the increase in mean particle size from 0.11 to 0.15-0.195 µm.

In order to examine the particle distribution according to size, fractionation of the medium to be examined was used. The emulsions were centrifuged under mild conditions (1500 rpm) and separated (precisely) into 3 fractions: an upper fraction of 20%, a middle fraction of 60% and a lower fraction of 20% of the sample volume (FIG. 1). As can be detected from FIG. 1, the carbon emulsion serving as prototype has, apart from the three fractions which differ according to particle size, a light fraction, which contains the free phospholipids, as result of which weak bonds of the absorption layer to oil phase and the surfactants which are not bonded in the absorption layer are established. For each fraction, values for a and n were measured. The mentioned parameters for fractionated emulsions of the composition according to the invention are indicated in Table 9 with storage of 1-12 months. It emerged that n and a display no change during storage for upper and middle fractions. In the case of the lower fraction, a slight increase in particle size with an increase in storage time was observed. This led to an extension in the distribution width of the particle size. The maximum distribution width was thereby in a range of 0.06-0.19 µm.

The obtained results established that the mean particle size of native and water-diluted emulsions (stress effect) increased slightly within 12 months and remained within the permissible limits below 0.20 µm.

TABLE 9

Parameters n and a which characterize the distribution width of the particle size for emulsions from examples 1, 3, 4, 5, 8 and 9 with storage of 12 months (upper, middle, lower = fractions after centrifugation)

| | | | N | | | a µm | | |
|---|---|---|---|---|---|---|---|---|
| Lot no. | t month | Dilution | upper | middle | lower | upper | middle | lower |
| 1-01 | 0 | undiluted | 3.50 | 3.27 | 3.27 | 0.105 | 0.119 | 0.124 |
| | | 1:2 | 3.87 | 3.39 | 2.93 | 0.05 | 0.114 | 0.157 |
| | 1 | undiluted | 3.47 | 3.27 | 3.0 | 0.107 | 0.124 | 0.148 |
| | | 1:2 | 3.57 | 3.43 | 3.13 | 0.095 | 0.111 | 0.136 |
| | 3 | undiluted | 3.43 | 3.33 | 2.93 | 0.11 | 0.119 | 0.157 |
| | | 1:2 | 3.83 | 3.30 | 3.23 | 0.062 | 0.121 | 0.128 |
| | 6 | undiluted | 3.47 | 3.27 | 3.0 | 0.106 | 0.124 | 0.148 |
| | | 1:2 | 3.9 | 3.4 | 3.13 | 0.044 | 0.114 | 0.136 |
| | 12 | undiluted | 3.47 | 3.27 | 2.78 | 0.107 | 0.124 | 0.185 |
| | | 1:2 | 3.6 | 3.33 | 2.93 | 0.09 | 0.119 | 0.156 |
| 1-03 | 0 | undiluted | 3.37 | 2.87 | 2.83 | 0.118 | 0.165 | 0.175 |
| | | 1:2 | 3.47 | 3.47 | 3.17 | 0.108 | 0.108 | 0.133 |
| | 1 | undiluted | 3.4 | 3.08 | 2.8 | 0.114 | 0.141 | 0.183 |
| | | 1:2 | 3.6 | 3.26 | 3.20 | 0.09 | 0.125 | 0.13 |
| | 3 | undiluted | 3.33 | 3.23 | 2.87 | 0.119 | 0.128 | 0.165 |
| | | 1:2 | 3.50 | 3.33 | 3.03 | 0.104 | 0.119 | 0.146 |
| | 6 | undiluted | 3.53 | 3.33 | 3.10 | 0.101 | 0.119 | 0.139 |
| | | 1:2 | 3.5 | 3.33 | 3.13 | 0.104 | 0.119 | 0.136 |
| | 12 | undiluted | 3.53 | 3.27 | 2.93 | 0.10 | 0.124 | 0.157 |
| | | 1:2 | 3.6 | 3.4 | 3.0 | 0.09 | 0.114 | 0.148 |
| 1-04 | 0 | undiluted | 3.33 | 3.07 | 3.07 | 0.119 | 0.141 | 0.141 |
| | | 1:2 | 3.3 | 3.17 | 3.13 | 0.121 | 0.131 | 0.136 |
| | 1 | undiluted | 3.2 | 3.13 | 2.93 | 0.13 | 0.136 | 0.157 |
| | | 1:2 | 3.33 | 3.23 | 3.03 | 0.119 | 0.128 | 0.145 |
| | 3 | undiluted | 3.27 | 3.03 | 2.74 | 0.124 | 0.146 | 0.195 |
| | | 1:2 | 3.3 | 3.2 | 2.8 | 0.121 | 0.13 | 0.182 |
| | 6 | undiluted | 3.33 | 3.17 | 2.76 | 0.119 | 0.132 | 0.195 |
| | | 1:2 | 3.50 | 3.20 | 2.93 | 0.104 | 0.13 | 0.157 |
| | 12 | undiluted | 3.17 | 3.07 | 2.8 | 0.132 | 0.141 | 0.182 |
| | | 1:2 | 3.33 | 3.20 | 2.93 | 0.119 | 0.13 | 0.157 |
| 1-05 | 0 | undiluted | 3.0 | 3.23 | 2.93 | 0.148 | 0.128 | 0.157 |
| | | 1:2 | 3.60 | 3.33 | 3.06 | 0.09 | 0.119 | 0.141 |
| | 1 | undiluted | 3.33 | 3.17 | 2.9 | 0.119 | 0.132 | 0.162 |
| | | 1:2 | 3.47 | 3.27 | 3.07 | 0.106 | 0.124 | 0.141 |
| | 3 | undiluted | 3.23 | 3.13 | 2.87 | 0.127 | 0.136 | 0.166 |
| | | 1:2 | 3.23 | 3.29 | 3.03 | 0.127 | 0.122 | 0.146 |
| | 6 | undiluted | 3.37 | 3.17 | 2.73 | 0.116 | 0.132 | 0.195 |
| | | 1:2 | 3.53 | 3.23 | 2.97 | 0.101 | 0.128 | 0.151 |
| | 12 | undiluted | 3.23 | 3.07 | 2.72 | 0.128 | 0.141 | 0.198 |
| | | 1:2 | 3.57 | 3.2 | 2.93 | 0.095 | 0.13 | 0.157 |
| 1-08 | 0 | undiluted | 3.40 | 3.37 | 3.27 | 0.114 | 0.116 | 0.124 |
| | | 1:2 | 3.40 | 3.40 | 3.20 | 0114 | 0.114 | 0.13 |
| | 1 | undiluted | 3.37 | 3.30 | 3.17 | 0.116 | 0.122 | 0.132 |
| | | 1:2 | 3.30 | 3.20 | 2.90 | 0.122 | 0.130 | 0.161 |
| | 3 | undiluted | 3.33 | 3.17 | 2.93 | 0.119 | 0.132 | 0.158 |
| | | 1:2 | 3.47 | 3.40 | 2.83 | 0.106 | 0.114 | 0.175 |
| | 6 | undiluted | 3.20 | 3.06 | 2.81 | 0.13 | 0.151 | 0.181 |
| | | 1:2 | 3.37 | 3.14 | 2.73 | 0.124 | 0.165 | 0.196 |
| | 12 | undiluted | 3.08 | 2.97 | 2.72 | 0.14 | 0.15 | 0.198 |
| | | 1:2 | 3.52 | 3.16 | 2.99 | 0.10 | 0.13 | 0.15 |
| 1-09 | 0 | undiluted | 3.27 | 3.13 | 2.87 | 0.124 | 0.136 | 0.167 |
| | | 1:2 | 3.27 | 3.30 | 2.83 | 0.125 | 0.122 | 0.175 |
| | 1 | undiluted | 3.03 | 3.0 | 2.77 | 0.146 | 0.149 | 0.188 |
| | | 1:2 | 3.30 | 3.03 | 2.93 | 0.122 | 0.139 | 0.157 |
| | 3 | undiluted | 3.13 | 3.07 | 2.73 | 0.136 | 0.141 | 0.196 |
| | | 1:2 | 3.17 | 3.10 | 3.0 | 0.132 | 0.138 | 0.148 |
| | 6 | undiluted | 3.11 | 3.01 | 2.78 | 0.147 | 0.156 | 0.185 |
| | | 1:2 | 3.40 | 3.17 | 2.34 | 0.124 | 0.136 | 0.162 |

TABLE 9-continued

Parameters n and a which characterize the distribution width of the particle size for emulsions from examples 1, 3, 4, 5, 8 and 9 with storage of 12 months (upper, middle, lower = fractions after centrifugation)

| Lot no. | t month | Dilution | N upper | N middle | N lower | a μm upper | a μm middle | a μm lower |
|---|---|---|---|---|---|---|---|---|
| | 12 | undiluted | 3.08 | 2.91 | 2.78 | 0.14 | 0.16 | 0.185 |
| | | 1:2 | 3.33 | 3.15 | 2.81 | 0.12 | 0.135 | 0.18 |

The observed enlargement with an increase in distribution width of particle sizes was caused by being found in emulsions with relatively large particles. During fractionation of the emulsions after 12 months storage, the particle size in the lower fraction increased from 0.12 to 0.198 μm. In total, the results are in agreement with the Ostwald decomposition mechanism (or molecular distillation). The proportion of such relatively large particles was so low (~10%) that this did not impair the increase in average particle size. It should be emphasized that only a uniform particle sedimentation was observed during fractionation of the emulsions, as a result of which the lack of free phospholipids is confirmed even after one year of storage. Hence, the particle distribution in emulsion remained monomodal. The obtained results indicate maintenance of a general structure of the obtained emulsions within 1-12 months of storage.

Interaction indices $K_\tau$ of the particles with blood serum are indicated in the following Table 10, the blood serum having been modified by addition of a 5% albumin solution in the ratio 1:1.

The interaction indices of the fluorocarbon emulsions with blood serum which characterize the emulsion microstructure showed a slight variation range with fluorocarbon emulsions with egg phospholipids for 12 months storage (serum-emulsion ratio 1:0.05 and 1:0.1). When increasing the ratio to 1:0.10, the variation range of $K_\tau$ and $K_{1/2}$ also widened. For fluorocarbon emulsions with soya phospholipids, a small variation range for $K_\tau$ remained only up to a 6 month storage. As was mentioned, the observed variations are more probably based on the fact that it is very complicated to standardize the serum mixture within test series with different storage times of the emulsions. At the same time, maintenance of the variation range for an interaction of the emulsion with the blood serum for each lot within specific and narrower limits indicates that the particle surface properties change little during long-term storage (6-9 months). The abrupt change of $K_\tau$ at the end of storage in the absence of free phospholipids in the emulsions can be caused by the occurrence of an additional interaction between the particles and the macromolecules of the serum. In order to check this assumption, experimental values and calculation values of the turbidity τ were calculated, which is an additional, independent parameter for evaluation of the structural totality of the fluorcarbon emulsions (Table 11) [13].

TABLE 10

Interaction indices of the emulsions with the blood serum for different storage times at a temperature of +4° C.

| | | τ | | Kτ | |
|---|---|---|---|---|---|
| | | Emulsion-serum ratio | | | |
| Lot no. | Storage | 1:0.05 | 1:0.1 | 1:0.05 | 1:0.1 |
| 1-02 | 0 | 0.8 ± 0.1 | 1.33 ± 0.03 | 3.8 ± 0.5 | 6.2 ± 0.2 |
| | 1 | 0.93 ± 0.06 | 1.4 ± 0.1 | 4.9 ± 0.3 | 7.2 ± 0.5 |
| | 3 | 0.97 ± 0.02 | 1.99 ± 0.003 | 3.50 ± 0.07 | 5.01 ± 0.02 |
| | 6 | 0.97 ± 0.01 | 1.63 ± 0.03 | 3.5 ± 0.4 | 3.4 ± 0.1 |
| | 9 | 1.23 ± 0.02 | 2.09 ± 0.03 | 3.7 ± 0.2 | 7.0 ± 0.1 |
| | 12 | 1.7 | 2.32 ± 0.01 | 7.2 ± 0.3 | 10.09 ± 0.1 |
| 1-03 | 0 | 0.77 ± 0.07 | 1.1 ± 0.1 | 3.3 ± 0.3 | 4.8 ± 0.4 |
| | 1 | 0.84 ± 0.05 | 1.29 ± 0.06 | 4.0 ± 0.3 | 6.6 ± 0.3 |
| | 3 | 1.0 ± 0.1 | 1.46 ± 0.05 | 3.6 ± 0.6 | 5.28 ± 0 |
| | 6 | 0.92 ± 0 | 1.53 ± 0 | 3.3 ± 0.4 | 3.19 ± 0.03 |
| | 12 | 1.33 ± 0 | 1.92 ± 0 | 4.0 ± 0.2 | 6.4 ± 0 |
| 1-04 | 0 | 1.00 ± 0.06 | 1.25 ± 0.08 | 5.4 ± 0.3 | 5.4 ± 0.4 |
| | 1 | 1.1 ± 0.2 | 1.67 ± 0.03 | 5.3 ± 0.9 | 8.9 ± 0.2 |
| | 3 | 1.15 ± 0 | 1.84 ± 0.06 | 4.4 ± 0.3 | 3.83 ± 0.06 |
| | 6 | 1.18 ± 0.02 | 1.97 ± 0.03 | 5.7 ± 0.8 | 10.7 ± 0.2 |
| | 9 | 1.83 ± 0.04 | 1.76 ± 0.02 | 4.2 ± 0.4 | 4.40. ± 0.04 |
| | 12 | 1.30 ± 0.04 | 2.22 ± 0.07 | 7.7 ± 0.5 | 13.9 ± 0.8 |
| 1-05 | 0 | 0.98 ± 0.05 | 1.56 ± 0.08 | 5.1 ± 0.2 | 8.0 ± 0.4 |
| | 1 | 1.1 ± 0.1 | 1.76 ± 0.02 | 4.3 ± 0.6 | 7.0 ± 0.1 |
| | 3 | 1.1 ± 0.3 | 1.90 ± 0.06 | 4.5 ± 0.8 | 8.3 ± 0.2 |
| | 6 | 1.18 ± 0.02 | 2.05 ± 0.07 | 5.7 ± 0.8 | 11.1 ± 0.4 |
| | 12 | 1.60 ± 0.01 | 2.91 ± 0.05 | 3.6 ± 0.3 | 7.2 ± 0.1 |
| 1-08 | 0 | 0.77 ± 0.05 | 1.15 ± 0 | 3.4 ± 0.4 | 5.4 ± 0.7 |
| | 1 | 0.95 ± 0.02 | 1.43 ± 0.03 | 4.0 ± 1.0 | 6.4 ± 0.3 |
| | 3 | 1.10 ± 0.1 | 1.57 ± 0.02 | 5 ± 1 | 8.7 ± 0.5 |
| | 6 | 1.4 ± 0.1 | 1.94 ± 0.03 | 3.3 ± 0.6 | 5.4 ± 0.5 |
| | 9 | 1.52 ± 0.03 | 2.68 ± 0.05 | 10 ± 2 | 19 ± 1 |
| | 12 | 1.38 ± 0.08 | 2.30 ± 0.03 | 11 ± 2 | 21.3 ± 0.9 |

TABLE 10-continued

Interaction indices of the emulsions with the blood serum for different storage times at a temperature of +4° C.

| | | $\tau$ | | $K\tau$ | |
|---|---|---|---|---|---|
| | | Emulsion-serum ratio | | | |
| Lot no. | Storage | 1:0.05 | 1:0.1 | 1:0.05 | 1:0.1 |
| 1-09 | 0 | 0.81 ± 0.02 | 1.48 ± 0.03 | 5.6 ± 0.6 | 14.5 ± 0.3 |
| | 1 | 1.2 ± 0.1 | 1.8 ± 0 | 6 ± 1 | 4.79 ± 0.07 |
| | 3 | 1.2 ± 0 | 1.4 ± 0.4 | 6.0 ± 0.5 | 7 ± 3 |
| | 6 | 1.2 ± 0.2 | 2.25 ± 0.03 | 2.8 ± 0.5 | 6.4 ± 0.5 |
| | 9 | 1.9 ± 0.1 | 3.24 ± 0.03 | 14 ± 2 | 24 ± 2 |
| | 12 | 1.52 ± 0.03 | 2.68 ± 0 | 12 ± 1 | 25.3 ± 0.7 |

From a hysical point of view $\tau$ means the sum of output losses of a light beam for disperse systems in the case of a few particles if cooperative effects and multiple dispersions are absent. The agreement of experimental and calculated values of $\tau$ for undiluted and water-diluted emulsions proves that the interaction between particles and macromolecules of the serum remains almost unchanged even after 9-12 months storage at a temperature of +4° C. The abrupt change of $K_\tau$ is therefore more likely to be connected with the fact that additional supramolecular structures of perfluorocarbons/phospholipids appear in the aqueous dispersant, the same ratio of fluorocarbons to phospholipids occurring as in the emulsions.

TABLE 11

Experimental values and calculated values of the turbidity for emulsions with different storage times

| Lot no. | | $\tau_{500}$ | | | |
|---|---|---|---|---|---|
| PFC | Storage | undiluted | | diluted 1:2 | |
| % by vol. | month | Experiment | Calculated | Experiment | Calculated |
| 1-02 | 0 | 9.9 | 10.0 | 4.6 | 4.7 |
| (10% by | 1 | 11.7 | 11.6 | 3.60 | 3.75 |
| vol.) | 3 | 12.2 | 12.0 | 3.91 | 4.02 |
| | 6 | 13.8 | 13.1 | 4.1 | 3.86 |
| | 9 | 13.8 | 14.0 | 4.29 | 4.37 |
| | 12 | 16.1 | 14.1 | 4.98 | 4.94 |
| 1-03 | 0 | 8.23 | 9.06 | 3.60 | 3.65 |
| (20% by | 1 | 9.66 | 10.2 | 3.07 | 3.11 |
| vol.) | 3 | 12.4 | 11.3 | 3.3 | 3.39 |
| | 6 | 13.3 | 11.55 | 3.57 | 3.57 |
| | 12 | 13.1 | 12.4 | 4.02 | 4.02 |
| 1-04 | 0 | 12.3 | 11.4 | 4.05 | 4.0 |
| (20% by | 1 | 13.8 | 13.2 | 4.6 | 4.5 |
| vol.) | 3 | 21.0 | 15.4 | 4.98 | 5.0 |
| | 6 | 16.1 | 15.5 | 5.5 | 5.5 |
| | 9 | 17.2 | 17.2 | 5.6 | 6.2 |
| | 12 | 20.9 | 19.9 | 6.8 | 6.5 |
| 1-05 | 0 | 12.88 | 13.11 | 4.22 | 4.38 |
| (5% by | 1 | 14.03 | 13.25 | 4.68 | 4.71 |
| vol.) | 3 | 19.1 | 16.9 | 5.6 | 5.56 |
| | 6 | 16.8 | 16.15 | 5.3 | 5.3 |
| | 12 | 18.9 | 18.5 | 5.4 | 4.5 |
| 1-08 | 0 | 8.97 | 8.74 | 2.91 | 2.81 |
| (40% by | 1 | 11.7 | 11.6 | 3.53 | 3.47 |
| vol.) | 3 | 13.8 | 13.6 | 4.14 | 4.0 |
| | 6 | 16.6 | 15.4 | 4.68 | 4.59 |
| | 9 | 21.8 | 18.9 | 5.6 | 5.6 |
| | 12 | 21.2 | 19.7 | 6.2 | 6.2 |
| 1-09 | 0 | 14.03 | 14.44 | 4.29 | 4.15 |
| (40% by | 1 | 19.3 | 17.5 | 5.75 | 5.61 |
| vol.) | 3 | 19.09 | 18.72 | 5.52 | 5.34 |
| | 6 | 21.8 | 18.2 | 6.13 | 8.71 |

TABLE 11-continued

Experimental values and calculated values of the turbidity for emulsions with different storage times

| Lot no. | | $\tau_{500}$ | | | |
|---|---|---|---|---|---|
| PFC | Storage | undiluted | | diluted 1:2 | |
| % by vol. | month | Experiment | Calculated | Experiment | Calculated |
| | 9 | 26.2 | 23.9 | 7.7 | 7.8 |
| | 12 | 26.9 | 25.5 | 4.91 | 4.3 |

Before something is mentioned about the advantages of the composition and production method according to this invention of the fluorocarbon emulsions, it should be emphasized that the main conditions for fulfilling the gas transport function of the emulsions when flowing in the blood flow are the maintenance of the corpuscular nature of the particles and no reactogenity. From the point of view of colloidal chemistry and biophysics, the passage of the emulsion into the bloodstream can be regarded as a stress effect which should lead to a change in the dispersant properties. This effect can lead to the following observations, namely to dilution of the emulsion and to a reduction in concentration of the free emulsifier in the dispersant (rapid phase). As a result of this process, weakening of the molecular bonds of the surfactants to the particle surface is effected (slow phase). This weakening of the bond of the surfactants to fluorocarbons is impaired yet more by the contact and interaction of the particles with plasma macromolecules, as a result of which the composition of the absorption layer or the particle destruction can be changed. The described sequence of the processes is a simplified representation.

In tests on this side, the dilution of the emulsions with water simulates the first phase, namely dilution of the emulsion and reduction in concentration of the free emulsifier around the particles. Examination of the interaction of the obtained emulsions with blood plasma simulates the second phase, namely an effect of contact of serum macromolecules on the properties of the particle surface. It emerged that even after storage within one year the emulsion particles maintain their microstructure, the dilution with water not affecting the particle size, as a result of which the strong bond of the absorption layer of the surfactants to the particle core, the perfluorocarbons, was confirmed. The interaction index of the emulsion particles with blood serum (within limits of measuring errors) also remained unchanged, as a result of which the maintenance of the particle surface properties was established. The calculation values $\tau$ (after fractionation) was in agreement with the experimental values (before fractionation), as a result of which maintenance of the particle nature (particle structure) and the absence of free phospholipids in the emulsions was confirmed after one year of storage.

The methodical approaches used significantly increase the accuracy of the prediction with respect to the stability of the emulsions when passing into the bloodstream. Results of parallel examinations of the stability and the determination of the reactogenity index (Ip) from several lots of identical composition serve as confirmation of what was said. The index Ip was determined according to method [3].

Example 10

Four lots of the same emulsions with a composition according to example 2 were produced: fluorocarbon basis 9±1% by volume, ratio PFD to PFOB 9:1, supplement of an organic liquid 20%, egg phospholipids 1% by weight, adjuvant (ricinus and soya oil 1:1) 8% of the egg phospholipid concentration.

In the following Table 12, values for n and a of these lots are represented with different storage times.

TABLE 12

Wavelength exponent n and average particle size a for emulsions of the same composition PFD/PFOB/Fl/egg-p with different storage times

| Lot no. | Storage (months) | n undiluted | a μm undiluted | n diluted | a μm diluted |
|---|---|---|---|---|---|
| 5-03 | 0 | 3.70 ± 0.03 | 0.08 | 3.81 ± 0.07 | 0.06(5) |
|  | 1 | 3.62 ± 0.03 | 0.09 | 3.83 ± 0.05 | 0.06(5) |
|  | 6 | 3.80 ± 0.04 | 0.07 | 3.76 ± 0.06 | 0.07(5) |
| 5-04 | 0 | 3.36 ± 0.02 | 0.117 | 3.58 ± 0.01 | 0.09 |
|  | 1 | 3.30 ± 0.04 | 0.122 | 3.53 ± 0.05 | 0.10(1) |
|  | 6 | 3.37 ± 0.05 | 0.117 | 3.08 ± 0.08 | 0.14 |
| 5-05 | 0 | 3.35 ± 0.05 | 0.116 | 3.47 ± 0.04 | 0.11 |
|  | 1 | 3.07 ± 0.07 | 0.141 | 3.24 ± 0.09 | 0.12(7) |
|  | 6 | 3.37 ± 0.03 | 0.117 | 3.13 ± 0.02 | 0.13(6) |
| 5-06 | 0 | 3.32 ± 0.02 | 0.12 | 3.35 ± 0.05 | 0.11(6) |
|  | 1 | 3.07 ± 0.07 | 0.141 | 3.09 ± 0.08 | 0.139 |
|  | 6 | 3.45 ± 0.04 | 0.108 | 3.26 ± 0.09 | 0.12(5) |

According to the obtained data, the mean particle average in all cases for native and water-diluted emulsions remained unchanged in the 6 months storage time, being in the range of 0.06-0.17 μm. The distribution width of the particle size for native and water-diluted emulsions of the indicated composition changed pratically not at all the indicated examination time (Table 13). The interaction index $K_\tau$ the obtained emulsions with modified blood serum with respect to the relative measurement error (±10%) varied within narrow limits (see following Table 14).

TABLE 14

Interaction index $K_\tau$ of the emulsions of the same composition PFD/PFOB/Fl/egg phospholipid with the blood serum modified with albumin (80%)

| Lot no. | Storage (months) | Ratio of serum to emulsion 1:0.05 | Ratio of serum to emulsion 1:0.1 |
|---|---|---|---|
| 5-03 | 0 | 2.28 | 3.37 |
|  | 1 | 2.34 | 3.70 |
|  | 6 | 2.60 | 4.00 |
| 5-04 | 0 | 3.76 | 6.00 |
|  | 1 | 3.63 | 5.62 |
|  | 6 | 4.05 | 6.03 |
| 5-05 | 0 | 4.0 | 5.56 |
|  | 1 | 4.33 | 6.06 |
|  | 6 | 4.53 | 6.1 |

TABLE 13

Wavelength exponent n and mean particle size a which characterize the distribution width of the particles according to size, during fractionation by means of centrifugation of the emulsions with the same composition PFD/PFOB/Fl/egg phospholipid

| Lot no. | Storage (months) | Water dilution | n upper | n middle | n lower | a μm upper | a μm middle | a μm lower |
|---|---|---|---|---|---|---|---|---|
| 5-04 | 0 | native | 3.53 | 3.47 | 3.21 | 0.10 | 0.11 | 0.13 |
|  |  | 1:2 | 3.77 | 3.63 | 3.27 | 0.07 | 0.09 | 0.124 |
|  | 1 | native | 3.53 | 3.51 | 3.19 | 0.101 | 0.104 | 0.132 |
|  |  | 1:2 | 3.85 | 3.66 | 3.26 | 0.06 | 0.085 | 0.125 |
|  | 6 | native | 3.61 | 3.46 | 3.15 | 0.089 | 0.109 | 0.135 |
|  |  | 1:2 | 3.61 | 3.12 | 2.9 | 0.089 | 0.136 | 0.160 |
| 5-05 | 0 | native | 3.71 | 3.43 | 3.17 | 0.079 | 0.110 | 0.132 |
|  |  | 1:2 | 3.88 | 3.67 | 3.31 | 0.055 | 0.084 | 0.120 |
|  | 1 | native | 3.60 | 3.30 | 3.05 | 0.094 | 0.122 | 0.145 |
|  |  | 1:2 | 3.72 | 3.35 | 2.78 | 0.078 | 0.122 | 0.184 |
|  | 6 | native | 3.56 | 3.34 | 2.90 | 0.098 | 0.118 | 0.162 |
|  |  | 1:2 | 3.53 | 3.15 | 2.71 | 0.101 | 0.135 | 0.20 |

TABLE 15

Reactogenity index of the emulsions of the same composition
PFD/PFOB/FI/egg phospholipid (for the test, a dispersion of the
egg phospholipid was used)

| Lot no. | Storage time (months) | | |
|---|---|---|---|
| | 0 | 1 | 6 |
| Egg phospholipid dispersion | 1.4 | — | — |
| 5-03 | 2.83 | 1.68 | 1.92 |
| 5-04 | 1.14 | 2.14 | 2.24 |
| 5-05 | 1.83 | 1.83 | 1.70 |
| 5-06 | 2.42 | 1.35 | 2.63 |

The introduced results confirm that the emulsions and the production method according to this invention allow high quality of the emulsion microstructure without this being impaired during storage in the non-frozen state and during a subsequent stress effect in vitro (water dilution, interaction with the blood serum enriched with albumin). The results of the reactogenity test of the same emulsion patterns totally confirm the results of the simulation tests. At no point in the examination, did the reactogenity index exceed the critical value 3 (see Table 15).

Example 11

The inactness of the structure and the examination of the reactogenity of emulsions with a low flurocarbon content of 5% by volume.

The emulsion had the following composition: PFD/PFOB 1:1, PFMHP 1% soya phospholipid 0.5%, soya oil as adjuvant 12%, distribution width of the particle size in the range of 0.03 to 0.12 μm, initial reactogenity 1.61. The changes in mean particle size of native and water-diluted, identical emulsions of four lots were examined (see Table 16) and the reactogenity after 6 months storage (see Table 17). As is detectable from the indicated data, the increase in particle size in the formulation which was used and the production method according to this invention ensure that a low reactogenity is obtained.

TABLE 16

Wavelength exponent n and mean particle size
a of native and water-diluted emulsions of the same
composition PFD/PFOB/FI/soya phospholipid

| Lot no. | Storage (months) | n undiluted | a μm | n water-diluted 1:2 | a μm |
|---|---|---|---|---|---|
| 6-02 | 1 | 3.27 ± 0.04 | 0.122 | 3.29 ± 0.03 | 0.123 |
| | 6 | 3.08 ± 0.09 | 0.138 | 3.18 ± 0.02 | 0.132 |
| 6-03 | 1 | 3.19 ± 0.01 | 0.13 | 3.28 ± 0.02 | 0.124 |
| | 6 | 3.06 ± 0.01 | 0.145 | 3.11 ± 0.03 | 0.138 |
| 6-05 | 1 | 3.31 ± 0.01 | 0.12 | 3.48 ± 0.01 | 0.105 |
| | 6 | 3.24 ± 0.01 | 0.126 | 3.39 ± 0.01 | 0.114 |
| 6-06 | 1 | 3.11 ± 0.03 | 0.137 | 3.23 ± 0.03 | 0.128 |

TABLE 17

Reactogenity Ip for emulsions with a low fluorocarbon content
after 6 months storage in the non-frozen state

| | Lot no. | | | |
|---|---|---|---|---|
| | 6-02 | 6-03 | 6-05 | 6-06 |
| Reactogenity | 1.87 | 2.00 | 1.36 | 1.8 |

Example 12

The long-term storage of the emulsion within 18 months, which contains 10% by volume of fluorocarbons, has a ratio PFD/PFOB 8:2, an organic liquid of 20%, an egg phospholipid of 2% and ricinus oil as adjuvant of 10%. The examination results of the mean particle size with different storage times and water dilutions are indicated in Table 18. The development of the interaction of the emulsion with the blood serum enriched up to 50% with albumin are indicated in Table 19.

TABLE 18

Wavelength exponent n and average particle size a
for native and water-diluted emulsions PFD/PFOB/FI/egg-p
with different storage time in the non-frozen state

| Lot no. | Storage (months) | N undiluted | a μm | n water-diluted 1:2 | a μm |
|---|---|---|---|---|---|
| 7-03 | 0 | 3.70 ± 0.03 | 0.08 | 3.81 ± 0.07 | 0.065 |
| | 1 | 3.62 ± 0.03 | 0.09 | 3.83 ± 0.05 | 0.065 |
| | 6 | 3.80 ± 0.04 | 0.07 | 3.76 ± 0.06 | 0.07 |
| | 18 | 3.81 ± 0.04 | 0.065 | 3.77 ± 0.06 | 0.07 |

TABLE 19

Interaction Kτ of the emulsion PFD/PFOB/FI/egg-p with the blood
serum modified with albumin (50%) with different storage times

| | | Kτ Ratio of serum to emulsion | |
|---|---|---|---|
| Lot no. | Storage (months) | 1:0.05 | 1:0.1 |
| 7-03 | 0 | 1.74 | 2.37 |
| | 1 | 1.68 | 2.25 |
| | 6 | 1.48 | 2.74 |
| | 18 | 1.22 | 1.78 |

As emerges from the above data, the obtained emulsion maintains measurable, physical-chemical properties. As a result of this fact, the reactogenity of the emulsion after 18 months storage is 1.5.

Example 13

Prototypes, Oxygent AF 0104 (producer Alliance Therapeutic, USA) and the emulsion produced according to the method according to this invention were compared with respect to their quality. The comparison was implemented as a function of the change in wavelength exponent and mean particle size with water dilution.

In the emulsions to be compared with a different absolute fluorocarbon content, the same ratio of fluorocarbons to phospholipids was maintained. The indicated emulsions differ according to the production method. As a result, the emulsion PFOB-2 (produced according to the method according to this invention) contains no free phospholipid phase (see FIG. 16) after centrifugation, the Oxygent and the prototype PFO-1 in the absorption layer comprising non-bonded and free phospholipids which float easily during centrifugation (see FIG. 1A). For this reason, the mean particle size for Oxygent is reduced to 0.35 to 0.15 during dilution of the emulsion with water, the phospholipid aggregates and the emulsion particles decomposing.

In the prototype emulsion (PFOB-1), such coarse aggregates obviously were missing. However their presence, apart from the centrifugation results, shows great differences between calculated and experimental turbidity parameters which are determined according to the additive rule for native and diluted emulsions. For the emulsions according to the production method according to this invention, practically complete agreement of the experimental and calculated turbidity values was observed (see Table 21). It should be noted that, from a physical point of view, the parameter to be determined represents the sum of the power losses of a light beam in individual particles if cooperative effects and multiple scattering are absent. No agreement of the experimental and calculated turbidity values for the Oxygent and the prototype confirms the non-fulfillment of the additive rule, i.e. that an additional interaction between the particles and the light flux in the mentioned disperse systems occurs. This interaction can be detected clearly in the water dilution of the Oxygent and prototype, as a result of which no homogeneity of the particle types is achieved but different micellar structures of phospholipids in addition to the particles of the fluorocarbon emulsions are achieved. For the emulsions PFOB-2 and PFD/PFOB (Lot no. 5-03), the interaction of the particles with the light flux fulfilled the additive rule even after one month of storage in the non-frozen state.

FIG. 1 illustrates a separation of the fluorocarbon emulsions in fractions as a function of the production method: A according to the prototype (the emulsion contains free phospholipids), B according to the method according to this invention (the emulsion contains only particles of a different size). 1, 2, 3 mean the upper, middle and lower fraction. 1a means the free phospholipids in the upper fraction.

TABLE 21

Agreement of experimental and calculated turbidity values according to the additive rule

| Preparation | undiluted | | water-diluted 1:1 | |
|---|---|---|---|---|
| | Test | Calculation | Test | Calculation |
| Oxygent | 133.9 ± 1.0 | 33.2 | 59.3 ± 0.5 | 23 |
| PFOB-1 (prototype) | 26.6 ± 0.3 | 18.6 | 16.4 ± 0.2 | 5.21 |
| PFOB-2 (method according to this invention) | 9.3 | 10.0 | 2.35 | 2.31 |
| PFD/PFOB 9:1 (composition and method according to this invention, example 10) | 12.9 | 11.2 | 3.24 | 3.17 |

Hence the indicated examples show an entire series of advantages of the described composition and of the described production method of the emulsion according to this invention in comparison with the prototypes and the emulsions closest to the invention. This is possible because of the subsequent synergy effects.

1. PFD and PFOB are selected as main components since these perfluorocarbons prove to be biologically acceptable according to their biological and physical-chemical properties and have a proven and rapid elimination rate from the organism, i.e. from the cells of the reticuloendothelial system, which accumulate fluorocarbon particles.

2. The common use of PFD and PFOB in the effective ratio leads to a mixed oil phase, the properties of which gradually change from the center to the periphery. This makes it possible to use poorly lipophilic and no hydrophilic tertiary amines in the ingredients which have a substantially lower vapor pressure (see Table 1) and hence reduce the diffusion of lipophilic molecules of PFD and PFOB into the aqueous phase. This slows down the rate of the main mechanism of

TABLE 20

Composition of different fluorocarbon emulsions, wavelength exponent n and mean particle size a for undiluted and water-diluted (1:1) emulsions

| Preparation PFC | Composition | | n | | a, μm | |
|---|---|---|---|---|---|---|
| | PFC wt./vol. | Phospholipid % by wt. | undiluted | Water dilution H$_2$O 1:1 | undiluted | Water dilution H$_2$O 1:1 |
| Oxygent AF 0104 (PFOB) | 90% by wt. 45% by vol. | 4 | 2.34 ± 0.04 | 2.93 ± 0.1 | 0.35 | 0.15 |
| Emulsion PFOB-1 (prototype) | 45% by wt. 22% by vol. | 2 | 2.91 ± 0.09 | 2.82 ± 0.10 | 0.16 | 0.18 |
| Emulsion according to the method according to this invention (composition according to prototype PFOB-2) | 20% 10% by vol. | 1 | 3.38 ± 0.02 | 3.33 ± 0.05 | 0.114 | 0.115 | emulsion decomposition, the Ostwald ripening, and increases the stability of the selected composition of the fluorocarbon emulsions.
3. The introduction of PFOB into the composition of the emulsions extends their oxygen absorption capacity with the same fluorocarbon content and contributes additional x-ray contrast properties.
4. PFOB/PFD and a mixture of tertiary amines contributes to a lower viscosity of the final form as a result of stronger bonding of the absorption layer of surfactants around the particles, as a result of which it becomes possible to exclude free micellar forms of phospholipids in the aqueous phase of the emulsions.
5. The use of oils of different physical-chemical properties in addition to the phospholipids promotes formation of a denser membrane-similar absorption layer around the particles with a smaller quantity of phospholipids and prevents micellar structures without fluorocarbons.
6. The properties of the water-salt medium used ensure a negative charge on the particle surface, as a result of which the coalescence of the particles during storage and transportation is prevented.
7. In addition to process-technological methods which ensure the production of a highly calibrated emulsion (with a narrow particle distribution), the above-mentioned methods weaken the molecular distillation and promote higher stability of the emulsions.
8. The missing aggregates of the particles and micellar forms of the phospholipids ensure the absorption property and the property of the emulsion which activates the complement in the bloodstream, as a result of which a low reactogenity is effected and an increased biocompatibility of the emulsions of the composition according to this invention is promoted.

III. Tests for the Biomedicinal use of the Emulsions According to the Invention are Indicated Subsequently.

Test 1

For the use of the emulsions for a massive blood replacement, a volume substitution with a fluorocarbon emulsion, produced according to example 1 (section II) was implemented with healthy Wistar rats with a weight of 250-300 g (n=20), with a Nembutal anaesthesia. The survival ability after a massive blood replacement and obtaining liver mitochondria after an equalization of the blood loss (see method [16]) was determined. In order to ensure the oncotic pressure after the massive blood replacement, the emulsion was mixed before infusion with a 20% human albumin in the ratio of 1 part albumin to 6 parts emulsion so that a final concentration of albumin of 3.5% was achieved (relative to the fact that the emulsion had 10% by volume of fluorocarbons). During the blood replacement, the rats inhaled an air enriched with oxygen up to $FiO_2=0.5$ which was supplied under a transparent Plexiglas hood. The hood covered the head of the animal which was fixed on its back. 3.5 ml blood were removed from the venous sinus (of the right vestibule) and 3.5 ml emulsion were injected into the venous sinus. After 10 minutes, 3.5 ml blood was removed and the same quantity of emulsion was injected. This procedure was repeated until the removed quantity of blood comprised on average at least 3.5% of the weight of the animal; for example the removed quantity of blood and the injected emulsion was respectively 8.8 ml for the weight of 250 g. Before and after the blood replacement, the haemoglobin in the peripheral blood, the partial pressure of oxygen and the pH value in the arterial and venous blood was determined. In this test series, the haemoglobin concentration after the blood replacement dropped on average by 1.9. In the control group (n=20), a solution of 0.15 mol sodium chloride and 3.5% albumin was injected instead of the emulsion. With the nuclear resonance spectrometer, the fluorocarbon content in the peripheral blood was determined. After the blood replacement, the animals were kept in a chamber to which air enriched with oxygen up to $FiO_2=0.5$ was supplied.

In the test group (with blood replacement), all the animals survived and the haemoglobin, erythrocyte and leucocyte values were returned within 5 days to the normal values. In the control group 3 animals died. After 5 days, all the animals were killed under a Nembutal anaesthesia and mitochondria were separated from the liver. The breathing of the liver mitochondria was registered polarimetrically in the closed, thermostatically operating cell at 27° C. It was established that the breathing rate in the active state (with ATP synthesis) and the ATP synthesis rate with oxidation of the NAD-dependent substrate by 3-hydrooxybutyrate reduced on average by 1.5 with 20% activation of the succinate oxidation. These data confirm huge ischaemic damage. In the liver mitochondria separated 5 days after the blood replacement, activation of all breathing rates and an ATP synthesis of on average 25% was observed, as a result of which massive hypoxia in the anamnesis was demonstrated.

Test 2

All treatments were implemented as in the previous example but with the use of a 20% fluorocarbon emulsion. The haemoglobin content was reduced threefold in comparison to the initial values, on average 65-70% by volume of the blood being replaced. The volume of the removed blood and the injected blood replacement agent was respectively 12.25 ml for the weight of 250 g. In the test group, all the animals survived and, in the control group, 5 animals died.

Test 3

All the treatments were implemented as in example 1. 5 animals of each group were killed however after 6 hours, one day and 3 days after the blood replacement. The liver mitochondria were separated and phosphorylating breathing was registered. In the control group, a rapid suppression of the breathing rate and phosphorylation with an oxidation of the NAD-dependent substrate and succinate of on average above 50% was observed, by which severe ischaemic damage to mitochondria is characterized. In the test group, 40% activation of the phosphorylating breathing was observed 6 hours after the blood replacement which was maintained for one day and was at most 25% 3 days after the blood replacement. Such changes characterize liver mitochondria which have been preserved and suffered from hypoxia and not from ischaemia.

Test 4

This test related to preservation of kidneys in dogs after a haemorrhagic shock. Preservation of the kidneys was ascertained by kidney resuscitation after a kidney transplant to the animal with both removed kidneys (the examination was implemented after special permission from the ethics committee of the Health Ministry) and also by an evaluation of the adenyl nucleotides and of the lactate and pyruvate content in the kidneys one hour after the blood replacement. 10 dogs were examined with respectively 5 dogs in each group.

Examination procedure: from the dog with a weight of 20 kg, 400 ml blood was removed in a jet from the thigh artery under an intubation anaesthesia with controlled breathing, as a result of which a rapid pressure drop (up to 50-60 mm QS), a doubled heart contraction and an increased lactate concentration in the plasma up to 20 mmol occurred. After one hour of blood removal, a blood replacement agent, the quantity of which exceeded the blood loss by 15% by volume, was supplied to the animal, namely a 10% carbon emulsion according to example 1 with an albumin supplement up to 3.5% (as in example 14) in the test group and the plasma expander polyglucine in the control group. After a further hour, the animals were killed and the kidneys removed. One was used for transplantation and the other for examining the energy exchange of the kidney tissue.

In the control group, the ratio of ATP to ADP reduced threefold and the energy charge ([ATP]+½[ADP])/([ATP]+[ADP]+[AMP]) to 0.45. In the test group (blood replacement by fluorocarbon emulsion), the ratio of ATP to ADP was reduced at most twice and energy charge to 0.65-0.70. The ratio of lactate to pyruvate in the kidney tissue increased in the control group to 25-30 and in the test group at most to 6.

In all cases, urination was observed in the receiver animals with transplanted kidneys of those dogs which were treated with the fluorocarbon emulsion, immediately after inclusion of the transplant in the bloodstream. In the control group, the development of reperfusion damage with rapid tissue oedema and complete blood flow stoppage (nephrosis) was observed in 2 cases out of 5. In three cases of the control group, the blood flow in the transplanted kidney was re-established. Urination was observed only after several hours.

These data prove that the treatment of haemorrhagic shock in dogs with use of the fluorocarbon emulsion according to this invention ensures better protection of the organs from ischaemic and subsequent reperfusion damage.

Test 5

This test concerned the use of the fluorocarbon emulsion produced according to example 2 in order to preserve perfused rabbit hearts. Before use (1-2 hours), 400 ml fluorocarbon emulsion was mixed with 200 ml isotonic solution of Krebs-Henseleit in the ratio 2:1. 80 ml of a 20% solution of serum albumin were added to 600 ml of the mixture. The control composition for comparative tests comprised 600 ml salt solution with a supplement of 7.2 g mannitol and 80 ml of a 20% albumin solution. These compositions were used as perfusion medium for preserving the rabbit heart. A Langendorff perfusion was implemented circulation-wise at 37° C. The time in which the frequency and the amplitude of the heart contraction was maintained was registered. For the control and tests, 8 hearts were used respectively. During use of the perfusion liquid on the fluorocarbon basis, the capacity for contraction of the isolated rabbit heart was maintained for at least 6-8 hours. During perfusion with the control composition however, a severe reduction in the frequency and amplitude of the contraction up to cardiac arrest was observed.

In conclusion, it should be mentioned that the advantages of the emulsion according to this invention in contrast to the prototype and the emulsions which are closest to this invention are as follows.

The formulation and the production method according to this invention of the fluorocarbon emulsions ensure a finely distributed, calibrated emulsion with prescribed particle size in the range between 0.06 and 0.195 μm which contains 2 to 40% by volume of the fluorocarbon compounds and is stabilized with a phospholipid dispersion in a biologically acceptable water-salt solution. Production of a high degree of fineness and microstructure of the fluorocarbon emulsions with storage for 18 months in the non-frozen state was demonstrated, as a result of which it is made possible to obtain high biocompatibility which is expressed in low reactogenity. The developed emulsions are applicable for biomedicinal purposes, namely for the replacement of massive blood losses, for treating haemorrhagic shocks, for preventing ischaemic reperfusion damage, for preparing organs for transplants and for perfusion preservation of isolated organs. The developed emulsions have highly pronounced oxygen transport and rheological properties, which ensure prevention and elimination of ischaemic damage to oxygen-dependent mitochondrial functions and also support of the aerobic energy exchange in tissues during blood replacement and a treatment for haemorrhagic shocks.

Footnotes
1. Periodical of the Russian Mendeleyev Chemistry Association, 1985, volume 30, no. 4, p. 387-394.
2. J. G. Rieses et al. Physiological Activity of fluorine-containing Compounds (Tests and Clinical Examinations), collection of scientific works, Puschtschino, 1995, p. 73-90.
3. M. B. Berkos, abridged dissertation . . . doctorate in medical science, Leningrad, 1991, 24 pages
4. J. G. Rieses, Chem. Rev., 2001, V. 101, no. 9, p. 2797-2914.
5. RU Patent 2162692, C1. 7 A61K31/02, 9/10, 1999
6. RU Patent 2199311, C1. 7 A61K9/107, 31/02, 2001
7. U.S. Pat. No. 3,778,381, 1973
8. U.S. Pat. No. 6,113,919, 2000
9. U.S. Pat. No. 4,866,096, A61K31/025, 1989
10. U.S. Pat. No. 5,374,624, A61K31/025, 1994
11. RU Patent no. 2088217, 6 A61K9/10, 31/02, 1997
12. Biophysics, 1998, volume 33, no. 1, p. 126-129
13. I. N. Kusnezowa, abridged dissertation . . . doctorate in biological science, St. Petersburg, 1999, 38 pages
14. Chemical-Pharmaceutical Periodical, 1987, no. 12, p. 1498-1503
15. Periodical for Physical Chemistry, 1993, volume 67, no. 9, p. 1884-1888
16. E. I. Majewskij, abridged dissertation . . . doctorate med. science, Moscow, 1998, 36 pages

The invention claimed is:

1. A perfluorocarbon emulsion for medicinal purposes, comprising:
a water-salt medium;
a phospholipid dispersion in the water-salt medium; and
a plurality of perfluorocarbon compounds homogenized with the phospholipid dispersion, the plurality of perfluorocarbon compounds including a composition of perfluorodecaline and perfluorooctylbromide used as a rapidly eliminated component and a perfluorocarbon supplement including a mixture of perfluorinated tertiary amines, wherein the mixture of perfluorinated tertiary amines contains a mixture of perfluorotripropylamine and coproducts thereof, the mixture of perfluorotripropylamine and coproducts thereof comprising cis- und trans-isomers of perfluoro-1-propyl-3,4-dimethylpyrrolidone and perfluoro-1-propyl-4-methylpiperidine.

2. The perfluorocarbon emulsion according to claim 1, wherein the emulsion has a mean particle size in a range of 0.06-0.2 μm upon storage of at least six months in a non-frozen state at a temperature of +4° C.

3. The perfluorocarbon according to claim 2, wherein the mixture of perfluorinated tertiary amines further comprises perfluoro-N-methylcyclohexylpiperidine and coproducts thereof.

4. The perfluorocarbon emulsion according to claim 1, comprising 2-40% by vol. of the plurality of perfluorocarbon compounds.

5. The perfluorocarbon emulsion according to claim 1, wherein a composition of rapidly eliminated perfluorocarbon compounds contains perfluorodecaline and perfluorooctylbromide in a ratio between 10:1 and 1:10.

6. The perfluorocarbon emulsion according to claim 1, wherein the perfluorocarbon supplement contains 1 to 50% of a total content of a composition of rapidly eliminated perfluorocarbon compounds.

7. The perfluorocarbon emulsion according to claim 1, wherein the mixture of perfluorinated tertiary amines contains in addition perfluoro-N-methylcyclohexylpiperidine and coproducts thereof.

8. The perfluorocarbon emulsion according to claim 1, further comprising the phospholipid dispersion in the water-salt medium in a concentration of 0.2 to 5% by weight.

9. The perfluorocarbon emulsion according to claim 1, wherein the phospholipid dispersion in the water-salt medium contains one of egg phospholipids, soya phospholipids, phospholipids or a mixture thereof.

10. The perfluorocarbon emulsion according to claim 1, wherein the phospholipid dispersion in the water-salt medium contains as adjuvant vegetable oil in a quantity of 1-15% of the total content of the phospholipids.

11. The perfluorocarbon emulsion according to claim 10, wherein soya oil serves as adjuvant.

12. The perfluorocarbon emulsion according to claim 10, wherein sunflower seed oil serves as adjuvant.

13. The perfluorocarbon emulsion according to claim 10, wherein ricinus oil serves as adjuvant.

14. The perfluorocarbon emulsion according to claim 10, wherein a mixture of the oils in an effective ratio in a form of one of a twofold mixture and a threefold mixture serves as adjuvant.

15. The perfluorocarbon emulsion according to claim 1, wherein the composition of the water-salt medium contains sodium salts and potassium salts of chlorides and phosphates and the monosaccharide mannitol in injection water.

16. The perfluorocarbon emulsion according to claim 1, wherein a concentration of components in the water-salt medium has an osmotic pressure in the range of 100-350 mosmol/l.

17. The perfluorocarbon emulsion according to claim 16, wherein a mean particle size is equal to or less than 0.2 μm and is in a range of 0.06-0.2 μm.

18. The perfluorocarbon emulsion according to claim 9, wherein the mixture of perfluorinated tertiary amines contains in addition perfluoro-N-methylcyclohexylpiperidine and coproducts thereof.

19. The perfluorocarbon emulsion according to claim 1, wherein a mean particle size is equal to or less than 0.2 μm and is in a range of 0.06-0.2 μm.

20. A method for producing a perfluorocarbon emulsion according to claim 1, the method comprising:
a first step of producing a phospholipid dispersion in a water-salt medium, a second step of homogenization of the perfluorocarbon compounds in the phospholipid dispersion, a third step of heat sterilization of the produced emulsion, and a fourth step of subsequent storage of at least 6 months in a non-frozen state at a temperature of +4° C.

21. The method according to claim 20, wherein the phospholipid dispersion in the water-salt medium is produced by homogenization at a high pressure of at least 100 atm with subsequent heat sterilization.

* * * * *